US012741977B2

(12) United States Patent
Achmatowicz et al.

(10) Patent No.: US 12,741,977 B2
(45) Date of Patent: Sep. 22, 2026

(54) METHYLATION OF MCL-1 COMPOUNDS

(71) Applicant: Amgen Inc., Thousand Oaks, CA (US)

(72) Inventors: Michal Achmatowicz, San Diego, CA (US); Sheng Cui, Lexington, MA (US); Tsang-Lin Hwang, Camarillo, CA (US); Neil Fred Langille, Sudbury, MA (US); Janine K. Tom, Thousand Oaks, CA (US); James E. Huckle, Moorpark, CA (US); Markian Stec, Moorpark, CA (US); Tian Wu, Newbury Park, CA (US); Sean P. Brown, Half Moon Bay, CA (US)

(73) Assignee: AMGEN INC., Thousand Oaks, CA (US)

( * ) Notice: Subject to any disclaimer, the term of this patent is extended or adjusted under 35 U.S.C. 154(b) by 1004 days.

(21) Appl. No.: 17/910,042

(22) PCT Filed: Mar. 30, 2021

(86) PCT No.: PCT/US2021/024779

§ 371 (c)(1),
(2) Date: Sep. 8, 2022

(87) PCT Pub. No.: WO2021/202452

PCT Pub. Date: Oct. 7, 2021

(65) Prior Publication Data

US 2023/0117777 A1 Apr. 20, 2023

Related U.S. Application Data

(60) Provisional application No. 63/084,367, filed on Sep. 28, 2020, provisional application No. 63/070,630,
(Continued)

(51) Int. Cl.
*C07D 519/00* (2006.01)
*A61K 31/553* (2006.01)
(Continued)

(52) U.S. Cl.
CPC ........ *C07D 519/00* (2013.01); *C07B 2200/13* (2013.01)

(58) Field of Classification Search
CPC ................ C07D 519/00; C07D 513/06; C07B 2200/13; C07B 2200/07; A61P 35/00; A61P 35/02; A61K 31/553
See application file for complete search history.

(56) References Cited

U.S. PATENT DOCUMENTS 4,522,811 A 6/1985 Eppstein et al.
6,358,971 B1 * 3/2002 Ezquerra-Carrera ........................ C07D 471/04 546/121

(Continued)

FOREIGN PATENT DOCUMENTS

EP 1963309 B1 * 11/2010 ........... C07D 403/10
JP 2018-199667 A 12/2018

(Continued)

OTHER PUBLICATIONS

Ho et al., Adsorptive removal of gaseous methyl iodide by triethylenediamine (TEDA)-metal impregnated activated carbons under humid conditions, J. Haz. Mat., 368, pp. 550-559 (Year: 2019).*

(Continued)

*Primary Examiner* — Alexander K. Showalter

(57) ABSTRACT

Disclosed herein is an improved process for the synthesis of compound (A): (A), or a salt or solvate thereof via methylation of compound (B): (B), or a salt or solvate thereof, a crystalline hydrate of compound A, and pharmaceutical formulations comprising a crystalline hydrate of compound (A).

40 Claims, 8 Drawing Sheets

Related U.S. Application Data filed on Aug. 26, 2020, provisional application No. 63/002,629, filed on Mar. 31, 2020.

(51) Int. Cl.

| | |
|---|---|
| ***A61P 35/00*** | (2006.01) |
| ***C07D 513/06*** | (2006.01) |

(56) References Cited

U.S. PATENT DOCUMENTS

| | | | |
|---|---|---|---|
| 6,468,798 | B1 | 10/2002 | Deb et al. |
| 6,471,996 | B1 | 10/2002 | Sokoll et al. |
| 6,472,375 | B1 | 10/2002 | Hoon et al. |
| 9,562,061 | B2 | 2/2017 | Brown et al. |
| 10,100,063 | B2 | 10/2018 | Brown et al. |
| 10,300,075 | B2 | 5/2019 | Brown et al. |
| 10,362,128 | B2 | 7/2019 | Kakehi |
| 10,494,381 | B2 | 12/2019 | Brown et al. |
| 10,500,213 | B2 | 12/2019 | Brown et al. |
| 10,821,115 | B2 | 11/2020 | Harrington et al. |
| 10,836,779 | B2 | 11/2020 | Brown et al. |
| 11,001,598 | B2 | 5/2021 | Lucas |
| 11,224,601 | B1 | 1/2022 | Harrington et al. |
| 11,274,105 | B2 | 3/2022 | Rescourio et al. |
| 11,279,712 | B2 | 3/2022 | Brown et al. |
| 11,306,107 | B2 | 4/2022 | Brown et al. |
| 11,364,248 | B2 | 6/2022 | Brown et al. |
| 11,685,747 | B2 | 6/2023 | Paras |
| 2009/0054402 | A1 | 2/2009 | Wang et al. |
| 2014/0051683 | A1 | 2/2014 | Wang et al. |
| 2015/0045357 | A1 | 2/2015 | Nikolovska-Coleska et al. |
| 2015/0284328 | A1 | 10/2015 | Wang et al. |
| 2017/0088560 | A1 | 3/2017 | Brown et al. |
| 2018/0289720 | A1 | 10/2018 | Harrington et al. |
| 2019/0016736 | A1 | 1/2019 | Brown et al. |
| 2019/0023720 | A1 | 1/2019 | Brown et al. |
| 2019/0352271 | A1 | 11/2019 | Chu |
| 2019/0381064 | A1 | 12/2019 | Harrington et al. |
| 2020/0171043 | A1 | 6/2020 | Harrington et al. |
| 2022/0257607 | A1 | 8/2022 | Kelly et al. |

FOREIGN PATENT DOCUMENTS

| | | | | |
|---|---|---|---|---|
| WO | 2008/131000 A2 | 10/2008 | | |
| WO | 2011/094708 A2 | 8/2011 | | |
| WO | 2013/052943 A2 | 4/2013 | | |
| WO | 2013/149124 A1 | 10/2013 | | |
| WO | 2016/033486 A1 | 3/2016 | | |
| WO | 2017/147410 A1 | 8/2017 | | |
| WO | WO-2018183418 A1 * | 10/2018 | ............. | A61P 35/02 |
| WO | 2019/036575 A1 | 2/2019 | | |
| WO | 2019/046150 A1 | 3/2019 | | |

OTHER PUBLICATIONS

Stewart et al., Experimental Chemotherapy Of Filariasis. Iv. The Preparation Of Derivatives Of Piperazine, J. Org. Chem., 13, pp. 134-143 (Year: 1948).*

Product Specification for 2-methyltetrahydrofuran, Sigma-Aldrich product No. 8.21093, obtained online at the url www.sigmaaldrich.com/specification-sheets/188/898/000000008210930000.pdf (Year: 2025).*

U.S. Appl. No. 17/501,075, Published as US 2023/0052348 on Feb. 16, 2023, Brown et al.

U.S. Appl. No. 17/910,042, Publsihed as US 2023/0117777 on Apr. 20, 2023, Achmatowicz et al.

U.S. Appl. No. 17/916,843, Published as US 2023/0136910 on May 4, 2023, Farrell et al.

U.S. Appl. No. 17/918,607, Not yet published (national phase of WO 2021/225823), Nov. 2021.

U.S. Appl. No. 17/920,084, Not yet published (national phase of WO 2021/226009), Nov. 2021.

U.S. Appl. No. 17/922,619, Not yet published (national phase of WO 2021/226168), Nov. 2021.

U.S. Appl. No. 17/923,015, Not yet published (national phase of WO2021/226168), Nov. 2021.

U.S. Appl. No. 18/022,905, Not yet published (national phase of WO 2022/046690), Mar. 2022.

U.S. Appl. No. 18/024,716, Not yet published (national phase of WO 2022/051317), Mar. 2022.

U.S. Appl. No. 18/038,579, Not yet published (national phase of WO 2022/115400), Jun. 2022.

U.S. Appl. No. 18/275,169, Not yet published (national phase of WO 2022/165240), Aug. 2022.

U.S. Appl. No. 18/296,211, Not yet published (national phase of PCT/US23/17505), Apr. 2023.

U.S. Appl. No. 18/296,215, Not yet published (national phase of PCT/US23/17504), Apr. 2023.

U.S. Appl. No. 18/313,703, Not yet published (national phase of WO2016/033486), Mar. 2016.

Tom Janine K. et al: "Implementing Continuous Manufacturing for the Final Methylation Step in the AMG 397 Process to Deliver Key Quality Attributes", Organic Process Research & Development, vol. 25, No. 3, Jan. 11, 2021.

Beroukhim,R., et al., "The landscape of somatic copy-No. alteration across human cancers," Nature 463, 899-905 (2010).

Lessene, G., et al., "BCL-2 family antagonists for cancer therapy," Nat. Rev. Drug. Discov., vol. 7, 989-1000 (2008).

Akgul, C., "Mcl-1 is a potential therapeutic target in multiple types of cancer," Cell. Mol. Life Sci. vol. 66 1326-1336 (2009).

Mandelin II, A. M. et al., "Myeloid cell leukemia-1 as a therapeutic target," Expert Opin. Ther. Targets, 11(3):363-373 (2007).

Rowe, R. C., et al., Handbook of Pharmaceutical Excipients, $5^{th}$ Edition (2005).

Berge, S. M. et al. "Pharmaceutical Salts", J. Pharm. Sci. 66: 1-19 (1977).

Hamajima, K. et al., "Intranasal Administration of HIV-DNA Vaccine Formulated with a Polymer, Carboxymethylcellulose, Augments Mucosal Antibody Production and Cell-Mediated Immune Response," Clin. Immunol. Immunopathol., 88(2), 205-210 (1998).

Higuchi, T. et al., "Pro-drugs as Novel Delivery Systems," vol. 14 of the A.C.S. Symposium Series (1975).

Roche, E.B., "Bioreversible Carriers in Drug Design", ed. Edward B. Roche, American Pharmaceutical Association and Pergamon Press, (1987).

Brubaker, J. D., et al., "A Practical, Enantioselective Synthetic Route to a Key Precursor to the Tetracycline Antibiotics," Org. Lett., 9, 3523-3525 (2007).

Krasovskiy, A et al., "Convenient Titration Method for Organometallic Zinc, Magnesium, and Lanthanide Reagents," Synthesis, 890-891 (2006).

Sigman, M. S. et al., "Palladium-Catalyzed Allylic Cross-Coupling Reactions of Primary and Secondary Homoallylic Electrophiles," J. Am. Chem. Soc., 134(28), 11408-11411 (2012).

International Search Report and Written Opinion of analogous PCT application PCT/US2018/02473 mailed on Jun. 4, 2018.

Farrell, R. P. "Breaking Symmetry Towards Development and Scale Up of a Complex Drug Candidate," American Chemical Society Meeting Presentation, Philadelphia, PA, Aug. 22, 2016.

Brown, B. "Interdiction at a Protein-Protein Interface: Structure-Based Design of Mcl-1 Inhibitors," American Chemical Society Meeting Presentation, Philadelphia, PA, Aug. 22, 2016.

Brown, S. "Interdiction at a Protein-Protein Interface: Structure-Based Design of Mcl-1 Inhibitors," Presentation at Caltech, Pasadena, CA, Jun. 1, 2016.

Brown, S. "Interdiction at a Protein-Protein Interface: Structure-Based Design of Mcl-1 Inhibitors," American Chemical Society Meeting Presentation, San Francisco, CA, Apr. 5, 2017.

Caenepeel, S. R. et al. "Preclinical Evaluation of AMG 176, A Novel, Potent and Selective Mcl-1 Inhibitor with Robust Anti-tumor Activity in Mcl-1 Dependent Cancer Models," Poster Presentation at American Association for Cancer Research Meeting, Washington DC, Apr. 1-5, 2017.

(56) References Cited

OTHER PUBLICATIONS

Hata, A. N. et al., "Combined targeting of MEK and MCL-1 induces apoptosis and tumor regression of KRAS mutant NSCLC," Poster Presentation at American Association for Cancer Research Meeting, Washington DC, Apr. 1-5, 2017.
Hata, A. N. et al., untitled structure slide, Poster Presentation at American Association for Cancer Research Meeting, Washington DC, Apr. 1-5, 2017.
Caenepeel, S. et al. "Preclinical Evaluation of AMG 176, A Novel, Potent and Selective Mcl-1 Inhibitor with Robust Anti-tumor Activity in Mcl-1 Dependent Cancer Models," Poster Presentation at American Association for Cancer Research Meeting, Chicago, IL, Apr. 14-18, 2018.
Caenepeel, S. et al. "Combined Inhibition of MCL1 and BCL-2 With AMG 176 and Venetoclax Induces Anti-tumor Effects in Acute Myeloid Leukemia," Poster Presentation at American Association for Cancer Research Meeting, Chicago, IL, Apr. 14-18, 2018.
Belmontes, B., "The Utilization of a Human MCL1 Knock-In Mouse Suggests that Reductions in B Cells and Monocytes may Serve as Clinically Relevant Pharmacodynamic markers of MCL1 Inhibition," Poster Presentation at American Association for Cancer Research Meeting, Chicago, IL, Apr. 14-18, 2018.
Brown, S. "Interdiction at a Protein-Protein Interface: Structure-Based Design of the Mcl-1 Inhibitor AMG 176," American Chemical Society Meeting Presentation, New Orleans, LA, Mar. 19, 2018.
Hughes, P. "The Discovery and Preclinical Characterization of AMG 176: A First-In-Class MCL-1 Inhibitor in Clinical Development for Multiple Myeloma," Poster Presentation at American Association for Cancer Research Meeting, Chicago, IL, Apr. 14-18, 2018.
International Preliminary Report on Patentability, PCT/2021/024779, issued by the European Search Authority dated Oct. 13, 2022.
International Search Report and Written Opinion, PCT/2021/024779, issued by the European Search Authority dated Jul. 28, 2021.
Takata, N. and Terada, K. Fundamentals and Applications of Crystal Polymorphism, Popular Edition, First Printing, CMC Publishing Co., Ltd., Oct. 22, 2010, pp. 105-117.

* cited by examiner

METHYLATION OF MCL-1 COMPOUNDS

CROSS REFERENCES TO RELATED APPLICATIONS

This application claims the benefit of U.S. Provisional Application No. 63/002,629, filed on Mar. 31, 2020, U.S. Provisional Application No. 63/070,630, filed on Aug. 26, 2020, and U.S. Provisional Application No. 63/084,367, filed on Sep. 28, 2020, which are each hereby incorporated by reference in their entireties and for all purposes as if fully set forth herein.

BACKGROUND

Technical Field

The present disclosure relates to processes for synthesizing (4S,7aR,9aR,10R,11E,14S,15R)-6'-chloro-10-methoxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H,17H)-trione (compound A), a salt, or solvate thereof, which functions as an inhibitor of myeloid cell leukemia 1 protein (Mcl-1), via methylation of ((4S,7aR,9aR,10R,11E,14S,15R)-6'-chloro-10-hydroxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H,17H)-trione, or a salt, or solvent thereof.

Description of Related Technology

The compound, (4S,7aR,9aR,10R,11E,14S,15R)-6'-chloro-10-methoxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16|6-cyclobuta[i][1,4]oxazepino[3,44][1,2,7]thiadiazacyclohexadecine-4,1'-naphthalene]-16,16,18(7H,17H)-trione (compound A), is useful as an inhibitor of myeloid cell leukemia 1 ("Mcl-1):

(A)

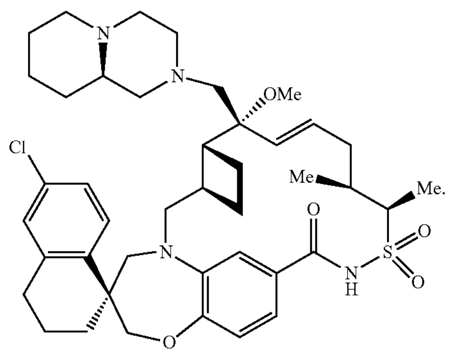

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions. Research has shown that Mcl-1 inhibitors can be useful for the treatment of cancers. MCI-1 is overexpressed in numerous cancers.

U.S. Pat. No. 10,300,075, which is incorporated herein by reference in its entirety, discloses compound A as an Mcl-1 inhibitor and provides a method for preparing it. However, improved synthetic methods that result in greater yield and purity of compound A are desired, particularly for the commercial production of compound A.

SUMMARY

In one aspect, disclosed herein is a process for synthesizing compound A, a salt, or a solvate thereof:

(A)

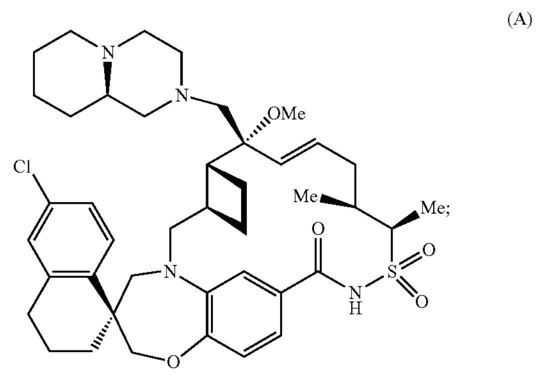

comprising:

(a) admixing: (i) a base selected from the group consisting of a non-nucleophilic base, an alkali metal hydride base, an alkali metal hydroxide base, an organolithium base, and any combination thereof; and (ii) a solution comprising compound B, a salt, or solvate thereof:

(B)

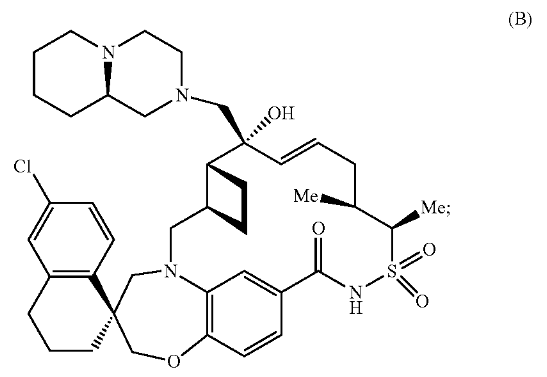

and an organic solvent comprising an ether solvent, a nonpolar solvent, or any combination thereof; and water, wherein the molar ratio of water to compound B is in a range of about 0.1:1 to about 3:1, to form a mixture; and (b) admixing the mixture of step (a) and MeX to form a mixture comprising compound A, wherein X is a halogen. In some embodiments, the process of the disclosure further comprising quenching the mixture of step (b) with a secondary amine base. In some cases, the secondary amine base is selected from the group consisting of N,N-diethylamine, morpholine, piperidine, pyrrolidine, piperazine, and combinations thereof. In various embodiments, each admixing step occurs at a temperature in a range of about 0° C. to about 40° C. In some cases, the temperature of each admixing step is in a range of about 15° C. to about 25° C.

In some embodiments, the base comprises lithium hexamethyldisilazide ("HMDS"), sodium HMDS, potassium HMDS, lithium diisopropylamide, sodium diisopropylamide, potassium diisopropylamide, lithium tert-butoxide, sodium tert-butoxide, potassium tert-butoxide, lithium tert-amylate, sodium tert-amylate, potassium tert-amylate, potassium hydride, sodium hydride, potassium hydroxide, sodium hydroxide, lithium hydroxide, 2,2,6,6-Tetramethylpiperidine (TMP), LiTMP, n-butyllithium (n-BuLi), n-hexyllithium, 1,1,3,3-tetramethylguanidine (TMG), 1,8-diazabicyclo[5.4.0]undec-7-ene (DBU), 1,5-diazabicyclo[4.3.0]non-5-ene, or any combination thereof. In some cases, the base comprises lithium hexamethyldisilazide HMDS, sodium HMDS, potassium HMDS, or any combination thereof. In embodiments, the base comprises potassium hexamethyldisilazide ("KHMDS").

In some cases, the molar ratio of the base to compound B is in a range of about 1:1 to about 5:1. In various cases, the molar ratio of the base to compound B is in a range of about 2.5:1 to about 4:1. In some embodiments, the molar ratio of the base to compound B is about 3.0:1 to about 3.5:1. In various embodiments, the molar ratio of the base to compound B is about 3.2:1.

In some cases, the organic solvent is selected from the group consisting of tetrahydrofuran ("THF"), 2-methyltetrahydrofuran, cyclopentyl methyl ether, tert-butyl methyl ether, 1,2-dimethoxyethane, toluene, hexane, heptane, 1,4-dioxane, and combinations thereof. In various cases, the organic solvent comprises THF.

In some embodiments, the molar ratio of water to compound B is in a range of about 0.5:1 to about 3:1. In various embodiments, the molar ratio of water to compound B is in a range of about 1:1 to about 3:1. In some cases, the molar ratio of water to compound B is about 1.4:1 to about 1.6:1.

In various cases, X is iodide. In some embodiments, the molar ratio of MeX to compound B is in a range of about 1:1 to about 4:1. In various embodiments, the molar ratio of MeX to compound B is about 2.7:1.

In some embodiments, the base is admixed with the solution in step (a) over a time period of about 5 seconds to about 6 hours. In various embodiments, the base is admixed with the solution in step (a) within 5 seconds. In some cases, the base is admixed with the solution in step (a) within 1 second. In some embodiments, the mixture of step (a) is stirred for about 1 second to about 12 hours. In various embodiments, the mixture of step (a) is stirred for about 1 second to about 20 minutes.

In some cases, the MeX is admixed with the mixture of step (a) over a time period of about 1 second to about 6 hours. In various cases, the MeX is admixed with the mixture of step (a) within 5 seconds. In some embodiments, the MeX is admixed with the mixture of step (a) within 1 second. In various embodiments, the mixture of step (b) is stirred for about 1 minute to 12 hours. In some cases, the mixture of step (b) is stirred for about 1 minute to about 20 minutes.

In some embodiments, compound B is a solvate. In various embodiments, compound B is a salt having a structure of compound B':

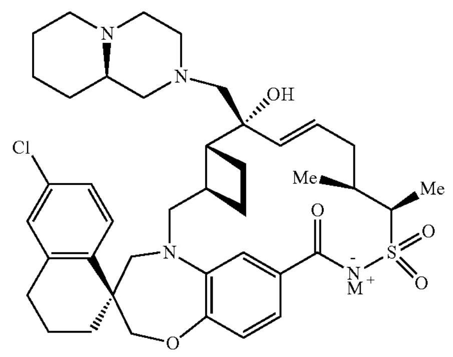

(B'), wherein M is an alkali metal. In some embodiments, the alkali metal is lithium, sodium, or potassium. In various embodiments, the alkali metal is potassium.

In some embodiments, compound B' is prepared by admixing compound B with an alkali hydroxide base and an organic solvent selected from the group consisting of an ether solvent, a nonpolar solvent, and any combination thereof, to form a mixture comprising compound B'. In various embodiments, the alkali hydroxide base is selected from the group consisting of potassium hydroxide, sodium hydroxide, lithium hydroxide, and combinations thereof. In some cases, the molar ratio of the alkali hydroxide base to compound B is in a range of about 0.5:1 to about 3:1. In various cases, the molar ratio of the alkali hydroxide base to compound B is about 1.5:1. In some embodiments, the organic solvent is selected from the group consisting of tetrahydrofuran ("THF"), 2-methyltetrahydrofuran, cyclopentyl methyl ether, tert-butyl methyl ether, 1,2-dimethoxyethane, toluene, hexane, heptane, 1,4-dioxane, and combinations thereof. In various embodiments, the organic solvent comprises THF. In some cases, the mixture comprising compound B' is stirred for about 1 hour to about 48 hours.

Also provided herein is a crystalline hydrate form of compound A, characterized by solid state $^{13}C$ NMR peaks at 13.57, 19.13, 20.39, 24.04, 25.54, 27.75, 30.09, 31.05, 36.84, 38.27, 39.48, 43.15, 49.53, 50.30, 51.84, 54.40, 56.15, 57.28, 57.78, 60.23, 61.80, 65.65, 78.05, 85.23, 115.91, 123.10, 124.60, 128.11, 130.53, 133.18, 133.87, 134.99, 139.72, 141.47, 143.08, 151.76, and 174.30±0.5 ppm.

Also provided herein are pharmaceutical formulations comprising the crystalline hydrate form of compound A as described herein and a pharmaceutically acceptable excipient.

Also provided herein are methods of treating a subject suffering from cancer, comprising administering to the subject a therapeutically effective amount of the pharmaceutical formulation comprising the crystalline hydrate form of compound A as described herein and a pharmaceutically acceptable excipient.

Also provided herein is a crystalline hydrate form of compound A, characterized by XRPD pattern peaks at 10.3, 16.3, and 17.1±0.2° 2θ using Cu Kα radiation.

Also provided herein are pharmaceutical formulations comprising the crystalline hydrate form of compound A as described herein and a pharmaceutically acceptable excipient.

Also provided herein are method of treating a subject suffering from cancer, comprising administering to the subject a therapeutically effective amount of the pharmaceutical formulation comprising the crystalline hydrate form of compound A as described herein and a pharmaceutically acceptable excipient.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

DETAILED DESCRIPTION

Figure 1:
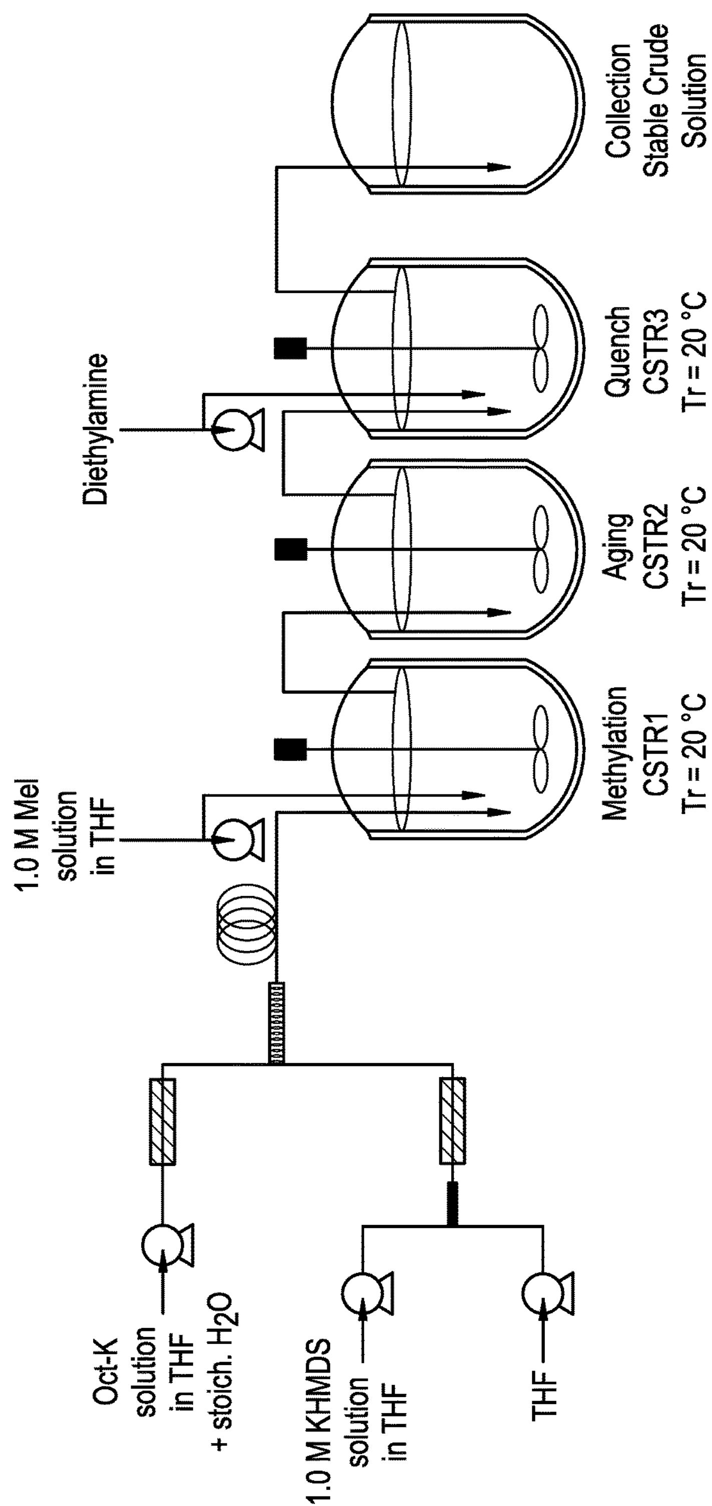
FIG. 1 depicts a diagram of an example flow chemistry process with a plug flow reactor and continuous stir tank reactors (CSTR), where compound B' (Oct-K) in THF with water, and potassium hexamethyldisilazide (KHMDS) are pumped into a plug flow reactor (residence time: 15 seconds), subsequent methylation in CSTR 1 (residence time: 5 min), additional aging in CSTR 2 (residence time: 5 min), and quenched in CSTR 3 (residence time: 5 min), as disclosed herein.

Disclosed herein are processes for synthesizing (4S,7aR,9aR,10R,11E,14S,15R)-6'-chloro-10-methoxy-14,15-dimethyl-10-{[(9aR)-octahydro-2H-pyrido[1,2-a]pyrazin-2-yl]methyl}-3',4',7a,8,9,9a, 10, 13, 14, 15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H, 17H)-trione (compound A), a salt, or a solvate thereof:

(A)

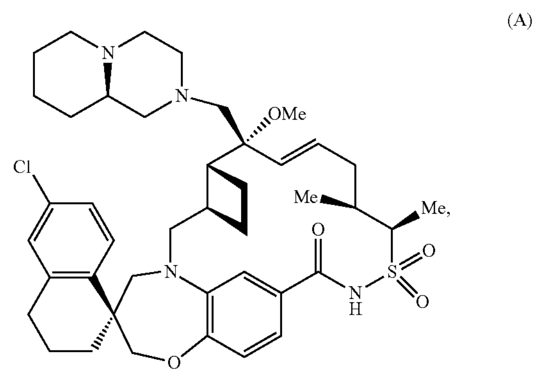

via methylation of ((4S,7aR,9aR,10R,11E,14S,15R)-6'-chloro-10-hydroxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H,17H)-trione (compound B), a salt, or solvate thereof:

(B)

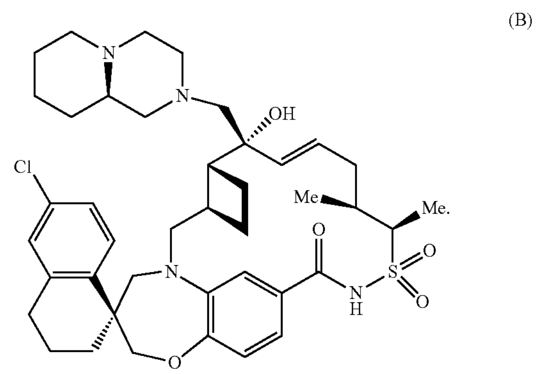

U.S. Pat. No. 10,300,075, which is incorporated by reference herein in its entirety, discloses synthetic procedures for synthesizing Mcl-1 inhibitors, such as compound A. The synthesis for compound A involves numerous steps, the last of which is a methylation of compound B to form compound A, as shown in Scheme 1, below.

Scheme 1.

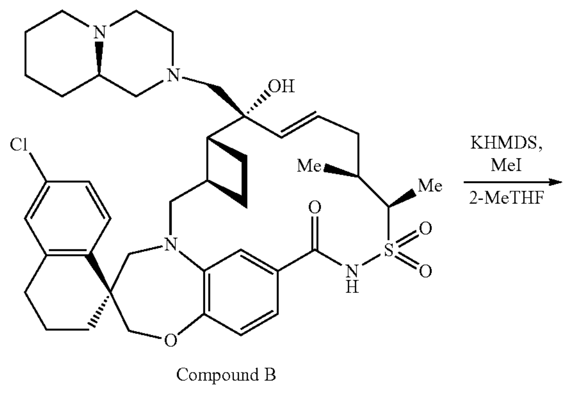

Compound B

-continued

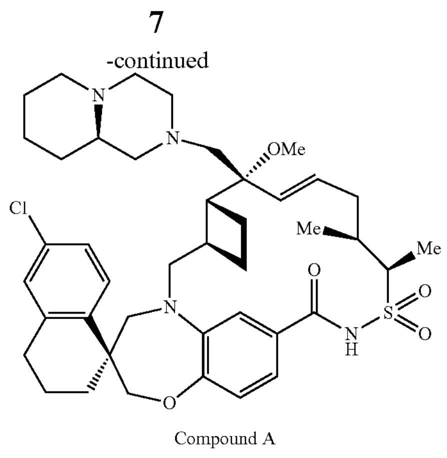

Compound A

The traditional methylation step to form compound A involves low temperatures, anhydrous reaction conditions, multiple charges of base (e.g., KHMDS) and MeI to reach full conversion of compound B, extended age time after the additions of the base and methyl iodide, a buffered quench step, and rigorous workup steps including silica gel column chromatography. Furthermore, the traditional methylation step results in excess impurities (e.g., a dimethylated compound, such as at the bridged nitrogen atom) that are difficult to remove during purification and lower yield. The traditional methylation step also has challenges with reproducibility and robustness.

In contrast, the process for methylating compound B, salt, or solvate thereof, to form compound A, as described herein, results in a drastically improved yield of compound A and a significant decrease in impurities (e.g., dimethylated product) in the final product. Furthermore, the process described herein is reproducible and robust, making it suitable for the production of commercial quantities of compound A, such as kilogram quantities. In particular, it has been found that the addition of water (e.g., stoichiometric addition of water) to the methylation reaction, and/or the rapid addition of base and/or methyl halide provides superior results with respect to yield, purity, reproducibility, and robustness.

As disclosed herein, the process for synthesizing compound A comprises: (a) admixing: (i) a base selected from the group consisting of a non-nucleophilic base, an alkali metal hydride base, an alkali metal hydroxide base, an organolithium base, and any combination thereof; and (ii) a solution comprising compound B, a salt, or solvate thereof:

(B)

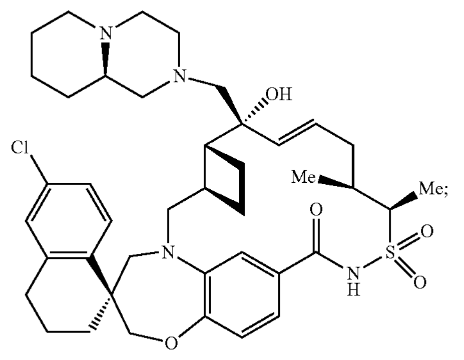

an organic solvent comprising an ether solvent, a nonpolar solvent, or any combination thereof and water, wherein the molar ratio of water to compound B is in a range of about 0.1:1 to about 3:1, to form a mixture; and, further admixing the mixture of step (a) and MeX to form a mixture comprising compound A, wherein X is a halogen (e.g., F, Cl, Br, or I), as shown in Scheme 2, below.

Scheme 2.

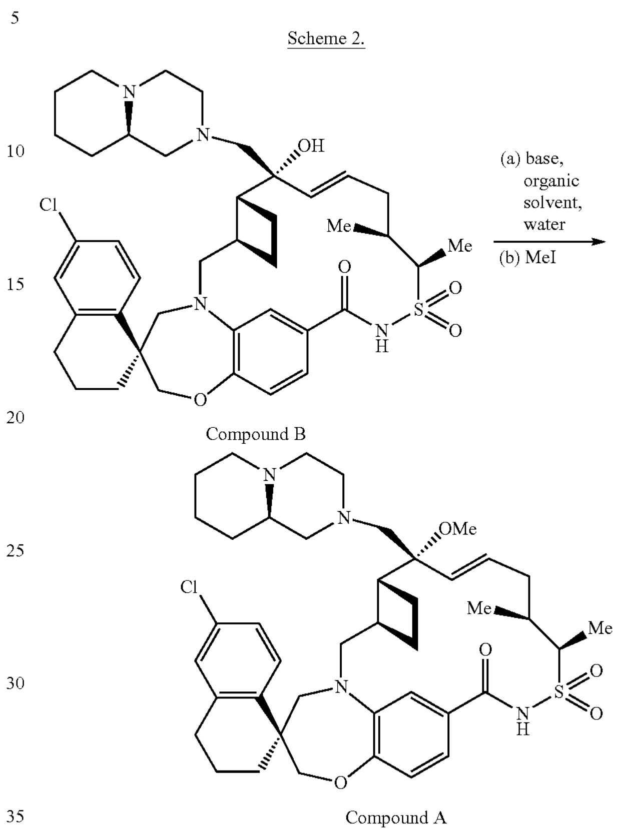

Compound B

Compound A

Further provided herein is a crystalline hydrate form of compound A, pharmaceutical formulations thereof, and methods of treating a subject suffering from cancer, comprising administering to the subject a therapeutically effective amount of the pharmaceutical formulation.

The compounds disclosed herein may be identified either by their chemical structure and/or chemical name herein. When the chemical structure and chemical name conflict, the chemical structure is determinative of the identity of the compound.

As known to those skilled in the art, compounds with a basic site and an acidic proton may exist as zwitterions. For example, compound A may be depicted as shown below

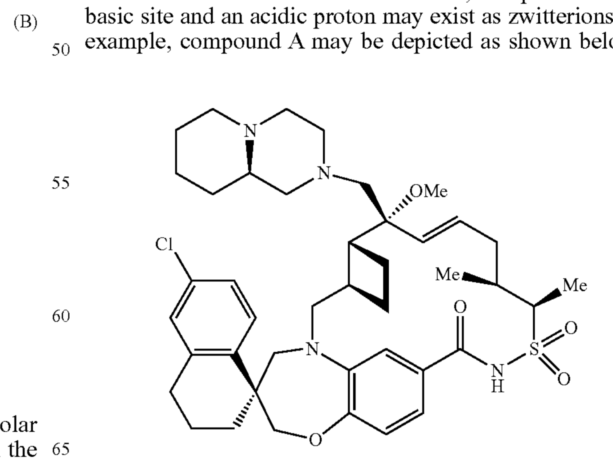

or may be depicted as the zwitterion as shown below

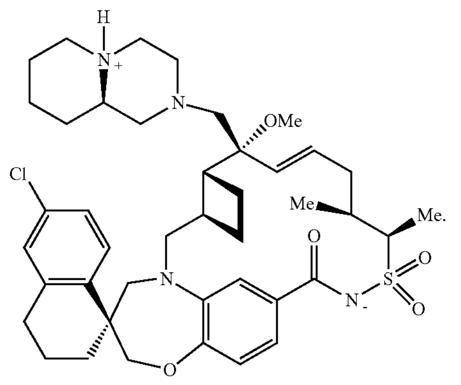

Because it is not possible to show both forms using the same structure, as used herein, reference to compound A or the first structure shown above will also refer to the zwitterion form shown in the second structure above. For example, the crystalline form described herein is believed to have compound A in the zwitterion form.

When ranges are used herein for physical properties, such as molecular weight, or chemical properties, such as chemical formulae, all combinations and subcombinations of ranges and specific embodiments therein are intended to be included.

As used herein, chemical structures which contain one or more stereocenters depicted with dashed and bold bonds (i.e., and ) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

The term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

"Treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of treatment, such as, for example, cancer.

The term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

"Pharmaceutically acceptable salts" include, but are not limited to salts with inorganic acids, such as hydrochlorate (i.e., hydrochloride), phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium. Those skilled in the art will recognize various synthetic methodologies that may be used to prepare non-toxic pharmaceutically acceptable addition salts.

The term "hydrate" refers to the chemical entity formed by the interaction of water and a compound, including, for example, hemi-hydrates, monohydrates, dihydrates, trihydrates, etc. Solvates of compound A used in formulations herein are within the scope of the invention. A hydrate, as used herein, can have a variable amount of water, such as, 0.6 to 2 water molecules per compound A molecule.

"Crystalline form" and "polymorph may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Process for Methylating Compound B to Form Compound A

In one aspect, provided herein is a process for preparing compound A via methylation of compound B, a salt, or solvate thereof. Compound A can be prepared from compound B, salt, or solvate thereof, in two steps according to Scheme 2, above. In the first step (step (a)), a base is admixed with a solution comprising compound B, a salt, or solvate thereof; an organic solvent comprising an ether solvent, a nonpolar solvent, or any combination thereof; and water; to form a mixture. In the second step (step (b)), the mixture of step (a) and methyl halide (MeX) are admixed to form a mixture comprising compound A. In some embodiments, compound B is provided as a solvate, such as a hydrate. In some embodiments, compound B is provided as a salt. Providing the salt form of compound B before methylation can result in increased solubility and consistency of reaction results. In some embodiments, compound B is provided as a salt having a structure of compound B':

(B')

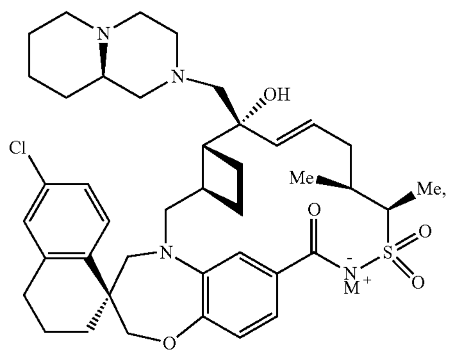

wherein M is an alkali metal. In embodiments, the alkali metal can be lithium, sodium, or potassium. In some embodiments, the alkali metal is potassium. Thus, in some embodiments, compound A can be prepared by methylating ((4S,7aR,9aR,10R,11E,14S,15R)-6'-chloro-10-hydroxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H,17H)-trione potassium salt (Compound B'), as shown in Scheme 3, below, wherein M is an alkali metal.

Scheme 3.

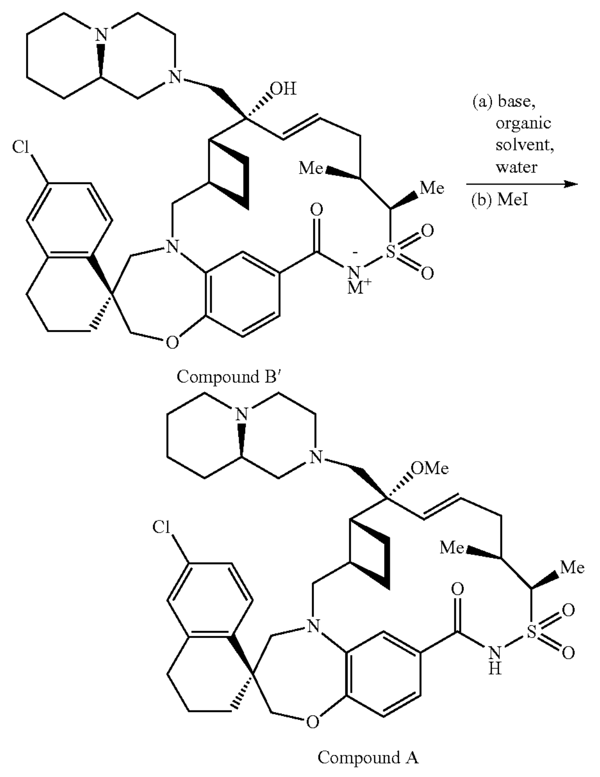

Compound B'

Compound A

Step (a)

The first step of the methylation process disclosed herein (step (a)) includes admixing (i) a base selected from the group consisting of a non-nucleophilic base, an alkali metal hydride base, an alkali metal hydroxide base, an organolithium base, and any combination thereof; and (ii) a solution comprising compound B, a salt, or solvate thereof; an organic solvent comprising an ether solvent, a nonpolar solvent, or any combination thereof; and water.

The base can be any base capable of deprotonating the —OH group of compound B. In some embodiments, the base can be selected from the group consisting of a non-nucleophilic base, an alkali metal hydride base, an alkali metal hydroxide base, an organolithium base, and any combination thereof. In some cases the base can be a non-nucleophilic base. Suitable non-nucleophilic bases can include, for example lithium hexamethyldisilazide ("HMDS"), sodium HMDS, potassium HMDS, lithium diisopropylamide, sodium diisopropylamide, potassium diisopropylamide, lithium tert-butoxide, sodium tert-butoxide, potassium tert-butoxide, lithium tert-amylate, sodium tert-amylate, potassium tert-amylate, 2,2,6,6-Tetramethylpiperidine (TMP), LiTMP, 1,1,3,3-tetramethylguanidine (TMG), 1,8-diazabicyclo[5.4.0]undec-7-ene (DBU), 1,5-diazabicyclo[4.3.0]non-5-ene, and any combination thereof. In embodiments, the non-nucleophilic base can be lithium HMDS, sodium HMDS, potassium HMDS, and any combination thereof. In some embodiments, the base can be an alkali metal hydride base. Suitable alkali metal hydride bases can include, for example LiH, NaH, KH, RbH, CsH, $BeH_2$, $MgH_2$, $CaH_2$, $SrH_2$, $BaH_2$, and any combination thereof. In embodiments, the alkali metal hydride base can be LiH, NaH, KH, or any combination thereof. In some cases, the base can an alkali metal hydroxide base. Suitable alkali metal hydroxide base can include, for example LiOH, NaOH, KOH, RbOH, CsOH, or any combination thereof. In some embodiments, the alkali metal hydroxide base can be LiOH, NaOH, KOH, or any combination thereof. In some cases, the base can be an organolithium base. Suitable organolithium bases can include, for example methyllithium, n-butyllithium, sec-butyllithium, isopropyllithium, tert-butyllithium, phenyllithium, or any combination thereof. In some embodiments, the organolithium base can be methyllithium, n-butyllithium, phenyllithium, or any combination thereof. In some cases, the base can comprise lithium hexamethyldisilazide ("HMDS"), sodium HMDS, potassium HMDS, lithium diisopropylamide, sodium diisopropylamide, potassium diisopropylamide, lithium tert-butoxide, sodium tert-butoxide, potassium tert-butoxide, lithium tert-amylate, sodium tert-amylate, potassium tert-amylate, potassium hydride, sodium hydride, potassium hydroxide, sodium hydroxide, lithium hydroxide, 2,2,6,6-Tetramethylpiperidine (TMP), LiTMP, n-butyllithium (n-BuLi), n-hexyllithium, 1,1,3,3-tetramethylguanidine (TMG), 1,8-diazabicyclo[5.4.0]undec-7-ene (DBU), 1,5-diazabicyclo[4.3.0]non-5-ene, or any combination thereof. In embodiments, the base can comprise lithium hexamethyldisilazide HMDS, sodium HMDS, potassium HMDS (KHMDS), or any combination thereof. In embodiments, the base is KHMDS.

In embodiments, the molar ratio of the base to compound B, a salt (e.g., compound B'), or solvate thereof, is in a range of about 1:1 to about 5:1, or about 2:1 to about 5:1, or about 2:1 to about 4:1, or about 2.5:1 to about 4:1, or about 3:1 to about 3.5:1. In some embodiments, the molar ratio of the base to compound B, a salt (e.g., compound B'), or solvate thereof can be about 1:1, 1.5:1, 2:1, 2.5:1, 2.6:1, 2.7:1, 2.8:1, 2.9:1, 3.0:1, 3.1:1 3.2:1, 3.3:1, 3.4:1, 3.5:1, 4:1, or 5:1 In some cases, the molar ratio of the base to compound B, a salt (e.g., compound B'), or solvate thereof can be about 3.2:1.

In embodiments, the organic solvent can comprise an ether solvent, a nonpolar solvent, or any combination thereof. In some cases, the organic solvent can be an ether solvent. Suitable ether solvents can include, for example, tetrahydrofuran (THF), 2-methyltetrahydrofuran (MeTHF), cyclopentyl methyl ether, tert-butyl methyl ether, 1,2-dimethoxyethane, 1,4-dioxane, diethyl ether, diisopropyl ether, bis(2-methoxyethyl) ether, propylene glycol methyl ether, or any combination thereof. In embodiments, the ether solvent can be THF or 2-methyltetrahydrofuran. In some cases, the organic solvent can be a nonpolar solvent. Suitable nonpolar solvents can include, for example, hexane, pentane, toluene, benzene, heptane, xylene, and any combination thereof. In embodiments, the nonpolar solvent can be toluene, hexane, heptane, or any combination thereof. In some cases, the organic solvent can be selected from the group consisting of THF, 2-methyltetrahydrofuran, cyclopentyl methyl ether, tert-butyl methyl ether, 1,2-dimethoxyethane, toluene, hexane, heptane, 1,4-dioxane, and any combination thereof. In some embodiments, the organic solvent comprises THF.

The process provided herein includes the addition of water to the solution of compound B, salt (e.g., compound B'), or solvate thereof, along with organic solvent in step (a), before the MeX is added in step (b). Adding water to step (a) of the process has been shown to drastically improve yield by 25% or more, improve the purity profile, and to reduce the aggregation of compound B, salt (e.g., compound B'), or solvate thereof during the methylation reaction. Without being bound by any particular theory, aggregates of compound B, salt (e.g., compound B'), or solvate thereof can potentially form through the interaction between the activated alkoxide (0) site of one molecule of compound B, salt (e.g., compound B'), or solvate thereof and the deprotonated sulfonamide ($N^-M^+$) site in another molecule of compound B, salt (e.g., compound B'), or solvate thereof. In addition, as the mixture of step (a) ages, the size of the aggregates increases. As a result, the activated alkoxide sites can be hindered, preventing MeX access to the activated hydroxyl group, leading to lower conversion. Aggregation with anhydrous solutions of step (a) occurs more rapidly than the solution containing water. Without being bound by theory, it is believed that adding water to step (a), can, in some embodiments, protect the activated alkoxide site by forming weak bonding, thus delaying aggregation initially, while allowing MeX access for productive methylation. Thus, in embodiments, the molar ratio of water to compound B, salt (e.g., compound B'), or solvate thereof, can be about 0.1:1 or more. In some embodiments, the molar ratio of water to compound B, salt (e.g., compound B'), or solvate thereof, can be in a range of about 0.1:1 to about 3:1, or about 0.5:1 to about 3:1, or about 1:1 to about 3:1, or about 1.5:1 to about 3:1, or about 1:1 to about 2:1, or about 1.2:1 to about 1.8:1, or about 1.4:1 to about 1.6:1. In embodiments, the molar ratio of water to compound B, salt (e.g., compound B'), or solvate thereof, can be about 1.5:1.

The base can be added to the solution in step (a) over a period of time or the base can be added to the solution in step (a) all at once. In some embodiments, the base is admixed with the solution in step (a) over a time period of about 5 seconds to about 6 hours, or about 5 seconds to about 1 minute, or about 5 seconds to about 10 minutes, or about 5 seconds to about 1 hour, or about 5 minutes to about 1 hour, or about 5 minutes to about 3 hours, or about 30 minutes to about 2 hours, or about 30 minutes to about 6 hours, or 2 hours to about 4 hours, or about 2 hours to about 3 hours, about 4 hours to about 6 hours, or about 3 hours to about 5 hours. In some embodiments, the base is admixed with the solution in step (a) over a time period of about 5 seconds, about 10 seconds, about 30 seconds, about 1 minute, about 5 minutes, about 10 minutes, about 30 minutes, about 1 hour, about 2 hours, about 3 hours, or about 6 hours. In embodiments, the base can be admixed with the solution in step (a) all at once. In some cases, the base is admixed with the solution in step (a) within about 5 seconds, within about 4 seconds, within about 3 seconds, within about 2 seconds, or within about 1 second.

In embodiments, the mixture of step (a) can be stirred for about 1 second to about 12 hours, or about 1 second to about 6 hours, or about 1 second to about 1 hour, or about 1 second to about 20 minutes, or about 1 second to about 10 minutes, or about 1 second to 15 minutes, or about 5 minutes to about 1 hour, or about 10 minutes to 2 hours, or about 30 minutes to about 2 hours, or about 2 hours to about 6 hours, or about 2 hours to about 10 hours, or about 5 hours to about 10 hours, or about 6 hours to about 12 hours. In some embodiments, the mixture of step (a) can be stirred for about 1 second, about 5 seconds, about 10 seconds, about 30 seconds, about 1 minute, about 5 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

In embodiments, step (a) can occur at a temperature in a range of about 0° C. to about 40° C., or about 15° C. to about 25° C. In embodiments, step (a) can occur at a temperature in a range of about 0° C. to about 40° C. or about 15° C. to about 25° C. In some embodiments, step (a) can occur at room temperature, such as about 20° C.

Step (b)

The second step of the methylation process disclosed herein (step (b)) includes admixing the mixture of step (a) and MeX to form a mixture comprising compound A, wherein X is a halogen.

X can be any of the halogens (e.g., F, Cl, Br, or I). In embodiments, X is fluoride. In some embodiments, X is chloride. In some embodiments, X is bromide. In some embodiments, X is iodide. In embodiments, the molar ratio of MeX (e.g., MeI) to compound B, salt (e.g., compound B'), or solvate thereof, is in a range of about 1:1 to 10:1, or about 1:1 to about 5:1, or about 1:1 to about 4:1, or about 1:1 to about 3:1, or about 2:1 to about 3:1, or about 2.5:1 to about 2.9:1. In embodiments, the molar ratio of MeX (e.g., MeI) to compound B, salt (e.g., compound B'), or solvate thereof, is about 1:1, 1.5:1, 2:1, 2.5:1, 2.6:1, 2.7:1, 2.8:1, 2.9:1, 3:1, 3.5:1, 4:1, 5:1, or 10:1. In some embodiments, the molar ratio of MeX (e.g., MeI) to compound B, salt (e.g., compound B'), or solvate thereof, is about 2.7:1.

The MeX (e.g., MeI) can be admixed with the mixture of step (a) over a period of time or the MeX can be admixed with the mixture of step (a) all at once. In some embodiments, the MeX is admixed with the mixture of step (a) over a time period of about 1 second to about 6 hours, or about 1 second to about 1 hour, or about 1 second to about 30 minutes, or about 1 second to about 10 minutes, or about 1 minute to 1 hour, or about 30 minutes to about 2 hours, or about 1 hour to about 3 hours, or about 3 hours to about 6 hours. In embodiments, the MeX can be admixed with the mixture of step (a) over a period of time of about 5 seconds, about 10 seconds, about 30 seconds, about 1 minute, about 5 minutes, about 10 minutes, about 30 minutes, about 1 hour, about 2 hours, about 3 hours, or about 6 hours. In embodiments, the MeX can be admixed with the mixture of step (a) all at once. In some embodiments, the MeX can be admixed with the mixture of step (a) within about 5 seconds, within about 4 seconds, within about 3 seconds, within about 2 seconds, or within about 1 second.

In embodiments, the mixture of step (b) can be stirred for about 1 second to about 12 hours, or about 1 second to about 6 hours, or about 1 second to about 1 hour, or about 1 second to about 20 minutes, or about 1 second to about 10 minutes, or about 1 second to 15 minutes, or about 5 minutes to about 1 hour, or about 10 minutes to 2 hours, or about 30 minutes to about 2 hours, or about 2 hours to about 6 hours, or about 2 hours to about 10 hours, or about 5 hours to about 10 hours, or about 6 hours to about 12 hours. In some embodiments, the mixture of step (b) can be stirred for about 1 second, about 5 seconds, about 10 seconds, about 30 seconds, about 1 minute, about 5 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

In embodiments, step (b) can occur at a temperature in a range of about 0° C. to about 40° C., or about 15° C. to about 25° C. In embodiments, step (b) can occur at a temperature in a range of about 0° C. to about 40° C. or about 15° C. to about 25° C. In some embodiments, step (b) can occur at room temperature, such as about 20° C.

Isolation and Purification of Compound A

The process disclosed herein for methylating compound B, a salt (e.g. compound B'), or solvate thereof, to form compound A can further comprise quenching the mixture of step (b) with a base. In embodiments, the base can be a secondary amine base. In some embodiments, the secondary amine base can be selected from the group consisting of N,N-diethylamine, morpholine, piperidine, pyrrolidine, piperazine, and any combination thereof. In some embodiments, the secondary amine base is N,N-diethylamine, morpholine, or any combination thereof. In embodiments, the molar ratio of the secondary amine base to compound B, salt (e.g., compound B'), or solvate thereof, can be in a range of about 5:1 to about 25:1, or about 10:1 to about 20:1, or about 12:1 to about 18:1, such as about 15:1.

Compound A can be isolated using any particular method suitable to one of ordinary skill in the art. In embodiments, compound A can be isolated from a crude solution by filtration, concentration of the filtrate under vacuum, and polish filtering the concentrated solution. Compound A can be purified by washing the polish filtered solution with a base (e.g., 5 N NaOH) and brine (e.g., 3×13 wt % NaCl) solution. In some embodiments, compound A can be isolated by filtration, concentration of the filtrate to about 0.01 M to about 0.5 M at about 40° C. under vacuum. The concentrated solution can be further polish filtered, and the polish filtered solution can be washed with an alkali metal base (e.g., about 5N NaOH) and brine (e.g., 3×13 wt % NaCl) solution.

Compound A can be further purified by any particular method suitable to one of ordinary skill in the art. In embodiments, compound A can be purified via distillation in an organic solvent or organic solvent mixture followed by crystallization from an organic solvent. Compound A can be filtered and dried under vacuum. In some embodiments, compound A can be purified via distillation in denatured ethanol with 0.5% to 5% v/v toluene (e.g., 2% v/v toluene) to concentrate the solution under vacuum. In embodiments, the distillation can be at a temperature in a range of 30° C. to about 100° C., for example 50° C., and the solution can be concentrated via distillation to about 0.01 M to about 0.5 M (e.g., about 0.13 M). In embodiments, compound A can be crystallized in an acetic acid solution by charging the concentrated solution from distillation with acetic acid. In embodiments, the acetic acid can be about 1 N to about 5 N (e.g., 3 N). In embodiments, the crystallization of compound A is accomplished via heating the concentrated solution of compound A with acetic acid to a temperature in a range of about 75° C. to about 85° C. for a period of time (e.g., about 15 minutes), optionally seeding the concentrated solution of compound A with crystals of compound A, followed by addition of acetic acid and heating of the seeded solution at a temperature in a range of about 75° C. to about 85° C. for a period of time (e.g., about 15 minutes), followed by cooling the solution to about room temperature (e.g., 20° C.) and aging the solution at about room temperature for a period of time (e.g., 1 hour or more). The aged crystallization solution is then filtered to yield purified compound A as the crystalline hydrate form described herein. In embodiments, the crystallization of compound A is accomplished via combining compound A with an ethanol/water mixture to form a crystallization mixture and heating the crystallization mixture to a temperature in a range of about 75° C. to about 85° C. for a period of time (e.g., about 15 minutes), optionally seeding the concentrated solution of compound A with crystals of compound A, followed by cooling the crystallization solution to about room temperature. The crystallization solution is then filtered to yield purified compound A as the crystalline hydrate from described herein. In embodiments, the crystallization of compound A is accomplished via combining compound A with about 10 volumes of a 95:5 ethanol/water to form a crystallization mixture and heating the crystallization mixture to a temperature in a range of about 75° C. to about 85° C. for a period of time (e.g., about 15 minutes), optionally seeding the concentrated solution of compound A with crystals of compound A, followed by cooling the crystallization solution to about room temperature. The crystallization solution is then filtered to yield purified compound A as the crystalline hydrate from described herein.

Crystalline Hydrate Form

Figure 7:
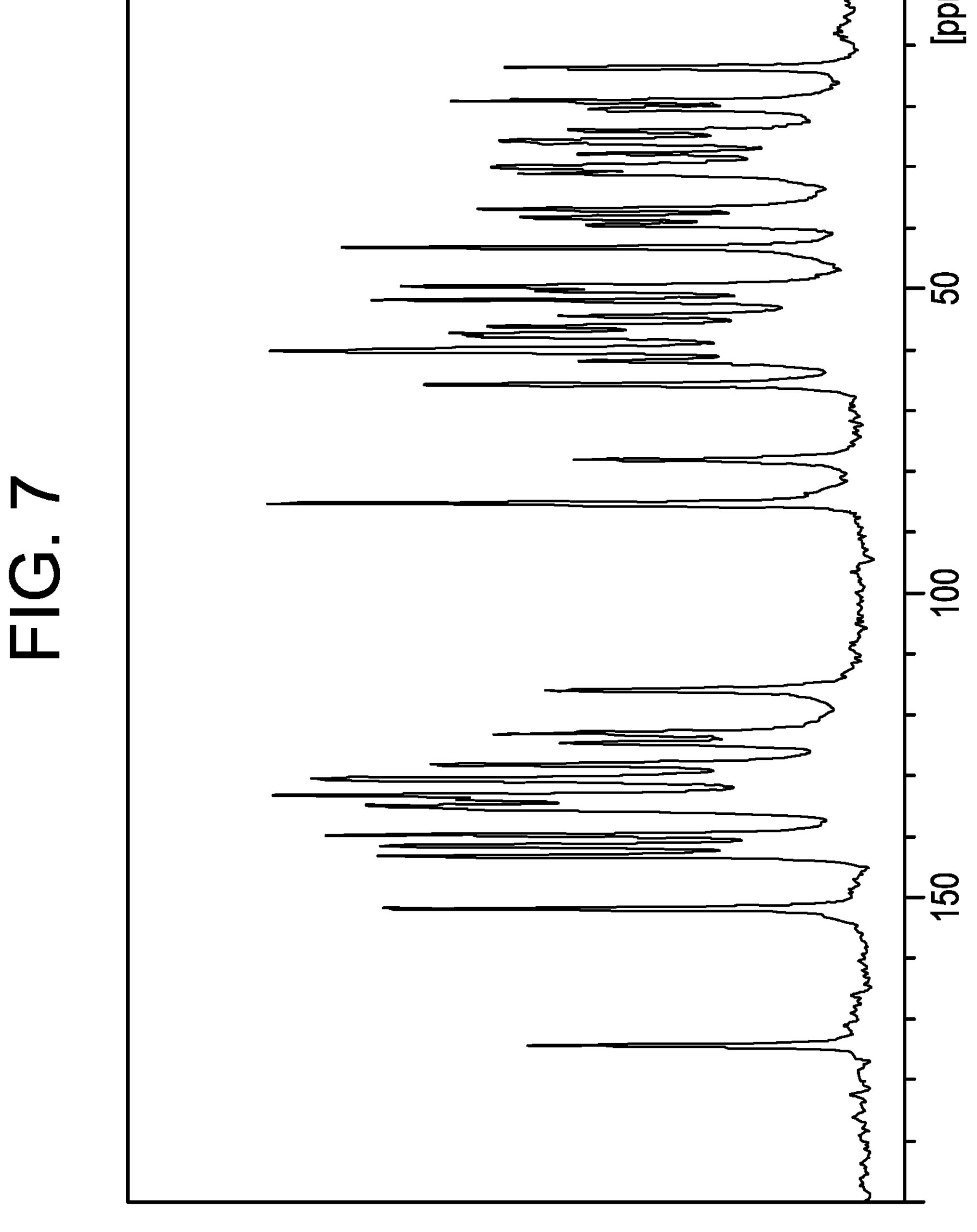
FIG. 7 depicts a solid state $^{13}C$ NMR of the crystalline hydrate form of compound A.

Also provided herein is a crystalline hydrate form of compound A. The crystalline hydrate form of compound A can be characterized by solid state $^{13}C$ NMR, obtained as set forth in the Examples, having peaks at 13.57, 19.13, 20.39, 24.04, 25.54, 27.75, 30.09, 31.05, 36.84, 38.27, 39.48, 43.15, 49.53, 50.30, 51.84, 54.40, 56.15, 57.28, 57.78, 60.23, 61.80, 65.65, 78.05, 85.23, 115.91, 123.10, 124.60, 128.11, 130.53, 133.18, 133.87, 134.99, 139.72, 141.47, 143.08, 151.76, and 174.30±0.5 ppm. In some embodiments, the crystalline hydrate form of compound A has a solid state $^{13}C$ NMR substantially as shown in FIG. 7, wherein by "substantially" is meant that the reported peaks can vary by ±0.5 ppm.

Figure 3:
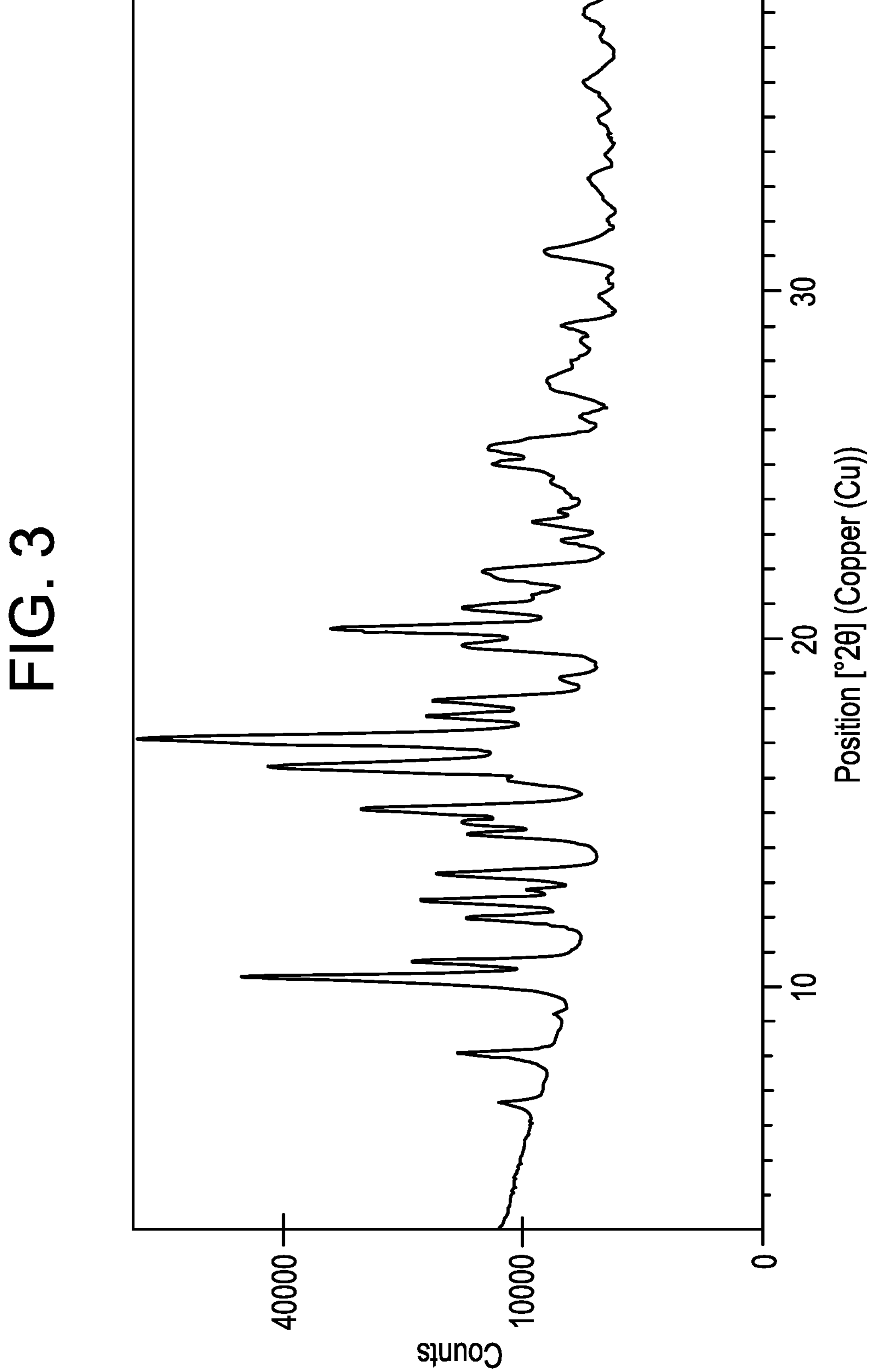
FIG. 3 depicts an X-ray powder diffraction ("XRPD") pattern of the crystalline hydrate form of compound A.

The crystalline hydrate form of compound A can be further characterized by an X-ray powder diffraction pattern, obtained as set forth in the Examples, having peaks at 10.3, 16.3, and 17.1±0.2° 2θ using Cu Kα radiation. The crystalline hydrate form of compound A optionally can be further characterized by an X-ray powder diffraction pattern having additional peaks at 8.23, 24.40, 25.03, 25.49, and 32.03±0.2° 2θ using Cu Kα radiation. The crystalline hydrate form of compound A optionally can be further characterized by an X-ray powder diffraction pattern having additional peaks at 14.4, 14.7, 15.9, 17.7, 18.1, 19.8, 20.9, 21.7, 21.9, and 25.0±0.2° 2θ using Cu Kα radiation. In some embodiments, crystalline hydrate form of compound A has an X-ray powder diffraction pattern substantially as shown in FIG. 3, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 4:
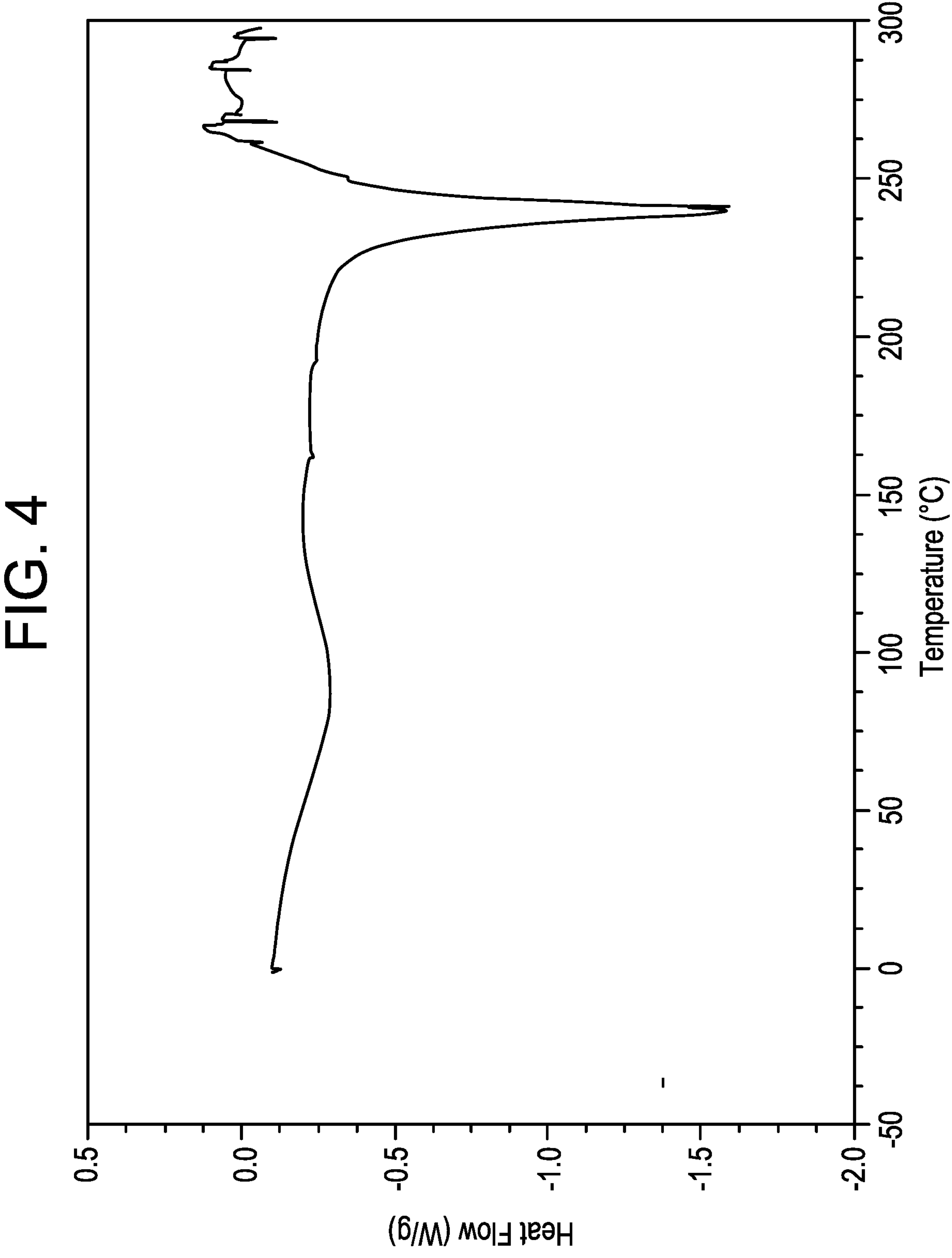
FIG. 4 depicts a DSC thermograph of the crystalline hydrate form of compound A.

Differential scanning calorimetry (DSC) thermographs were obtained, as set forth in the Examples, for the crystalline hydrate form of compound A. The DSC curve indicates an endothermic transition at 221° C.±3° C. Thus, in some embodiments, the crystalline hydrate form of compound A can be characterized by a DSC thermograph having a transition endotherm with an onset of 218° C. to 224° C. For example, in some embodiments the crystalline hydrate form of compound A is characterized by DSC, as shown in FIG. 4.

Figure 5:
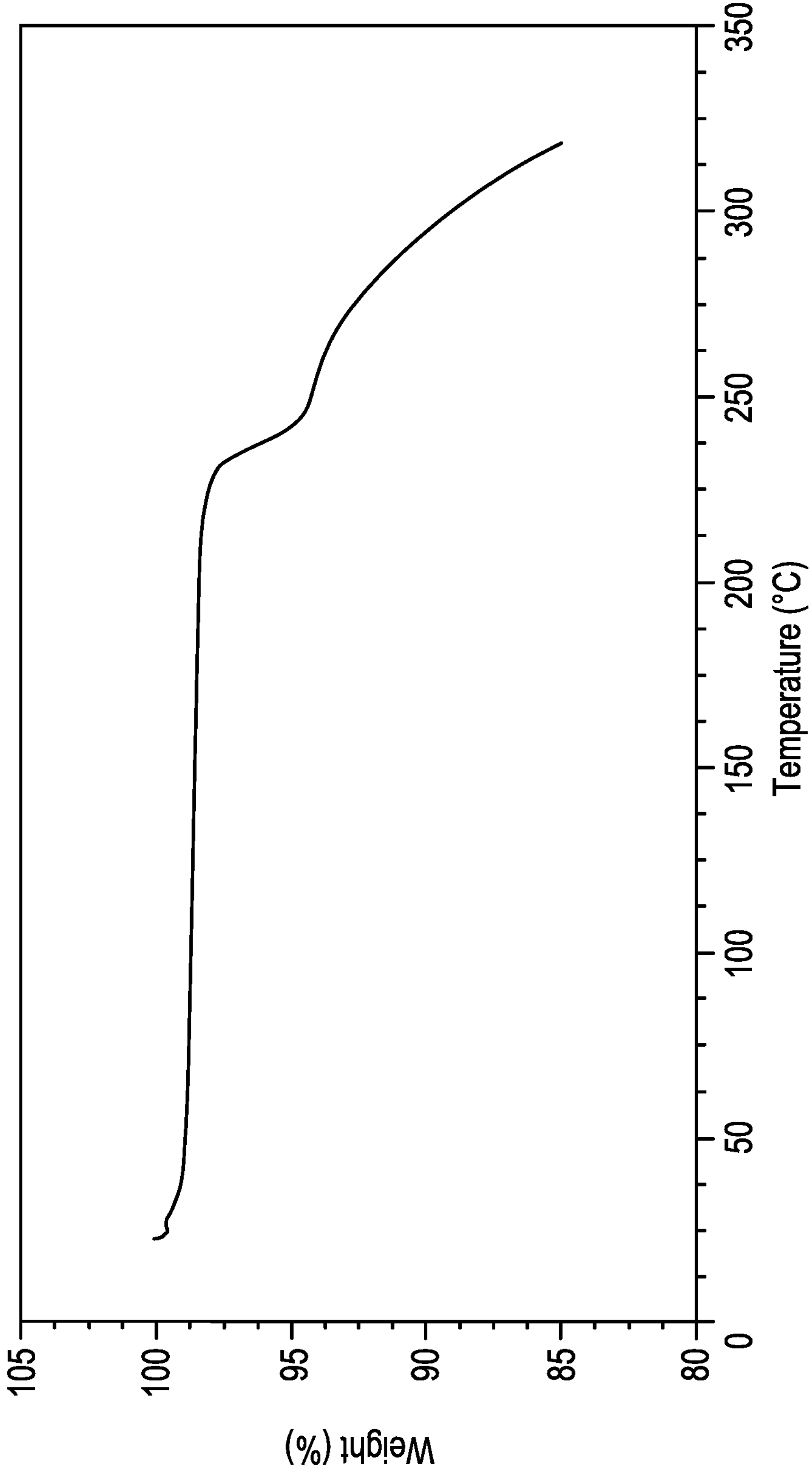
FIG. 5 depicts a TGA trace of the crystalline hydrate form of compound A.

The crystalline hydrate form of compound A also can be characterized by thermogravimetric analysis (TGA). Thus, the crystalline hydrate form of compound A can be characterized by a weight loss in a range of about 0% to about 3% with an onset temperature of 218° C. to 224° C. For example, the crystalline hydrate form of compound A can be characterized by a weight loss of about 2%, up to about 200° C. In some embodiments, the crystalline hydrate form of compound A has a thermogravimetric analysis substantially as depicted in FIG. 5, wherein by "substantially" is meant that the reported TGA features can vary by ±5° C.

Figure 6:
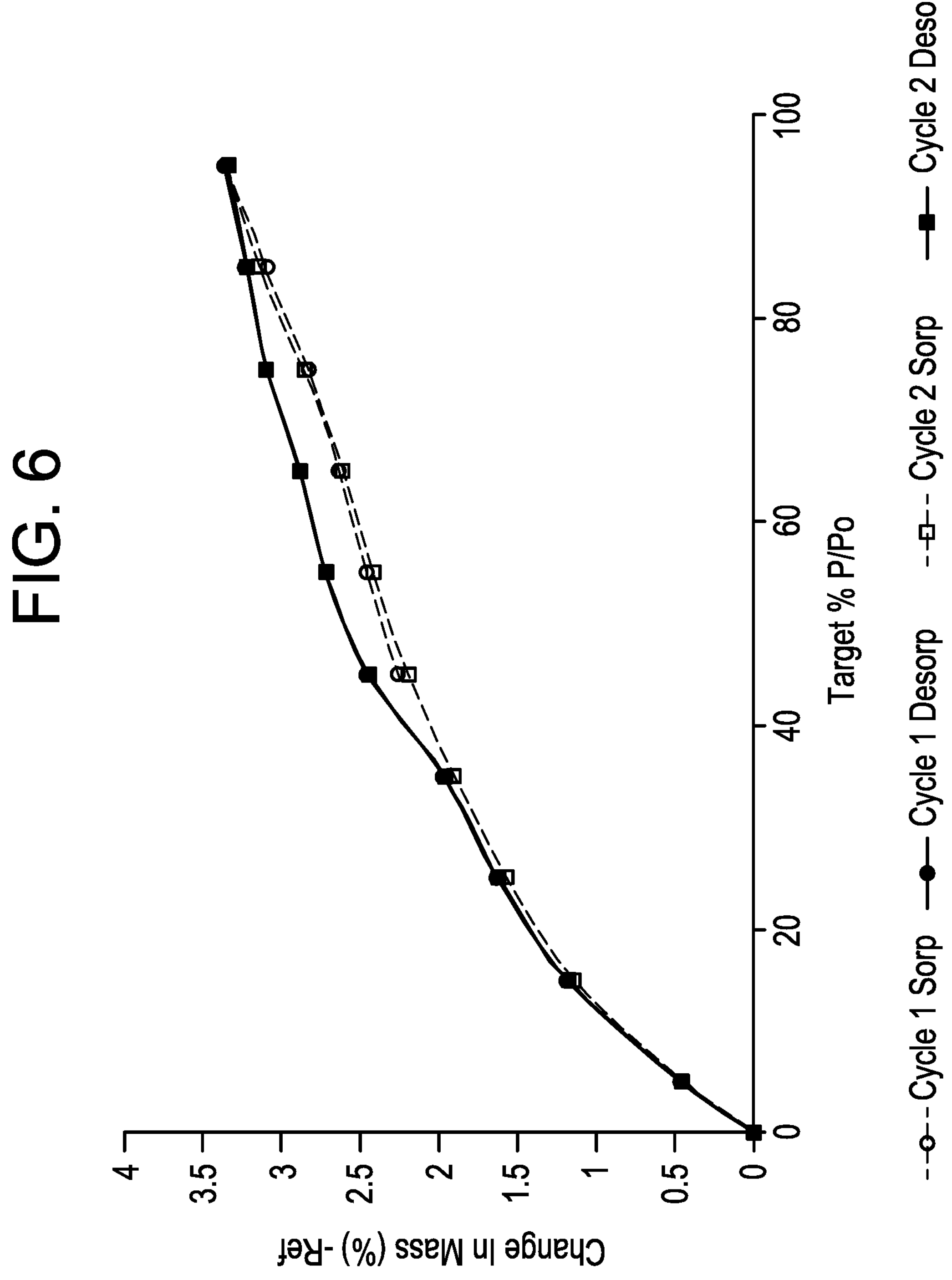
FIG. 6 depicts a moisture sorption profile of the crystalline hydrate form of compound A.

The crystalline hydrate form of compound A can be characterized by a moisture sorption profile. For example, in some embodiments the crystalline hydrate form of compound A is characterized by the moisture sorption profile as shown in FIG. 6, showing a weight gain of 3.3% by 95% RH.

Figure 8:
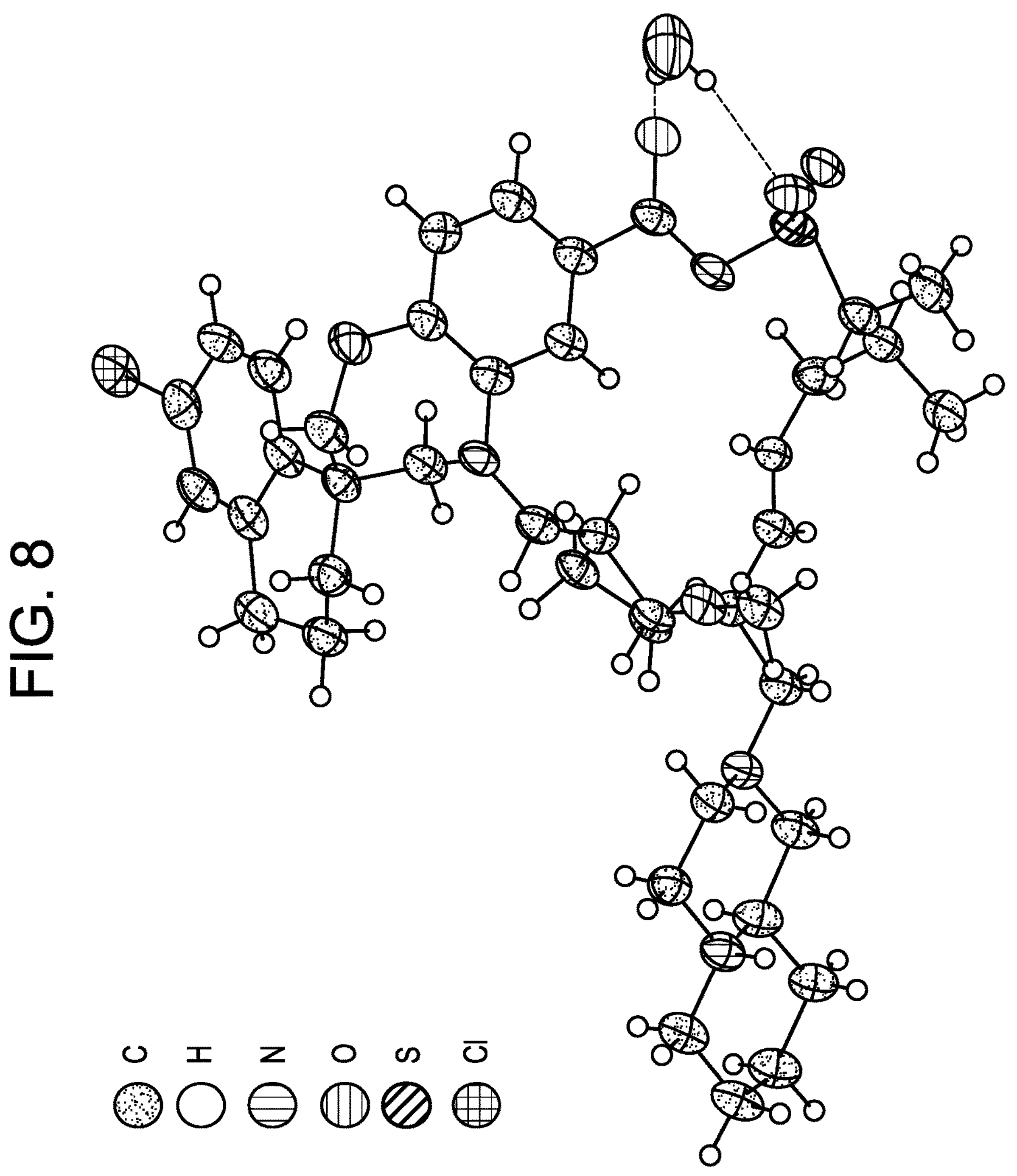
FIG. 8 depicts a single crystal X-ray crystal structure of crystalline hydrate form of compound A.

The crystalline hydrate form of compound A is further characterized by a single crystal structure substantially as shown in FIG. 8, or as set forth in the Examples.

Further provided herein are pharmaceutical formulations comprising the crystalline hydrate form of compound A as described herein and a pharmaceutically acceptable excipient. In some embodiments, the pharmaceutical formulation is in the form of a tablet. In some embodiments, the pharmaceutical formulation is in the form of an immediate release tablet.

Methods of Treating a Subject

Further provided herein are methods of treating a subject suffering from cancer, comprising administering to the subject a therapeutically effective amount of a pharmaceutical formulation as disclosed herein. In some embodiments, the cancer is multiple myeloma, non-Hodgkin's lymphoma, or acute myeloid leukemia.

Batch Chemistry

In some embodiments, the methylation of compound B, a salt (e.g., compound B'), or solvate thereof, to form compound A can be accomplished via batch chemistry.

In the batch process, compound A can be prepared from compound B, salt (e.g., compound B'), or solvate thereof, in two steps according to Scheme 2, above, and as previously described above.

In some embodiments, the first step of the batch process disclosed herein (step (a)) includes admixing (i) a base selected from the group consisting of a non-nucleophilic base, an alkali metal hydride base, an alkali metal hydroxide base, an organolithium base, and any combination thereof; and (ii) a solution comprising compound B, a salt (e.g., compound B'), or solvate thereof; an organic solvent comprising an ether solvent, a nonpolar solvent, or any combination thereof; and water. In some embodiments, the molar ratio of the base to compound B, a salt (e.g., compound B'), or solvate thereof, is in a range of about 1:1 to about 5:1. In embodiments, the molar ratio of water to compound B, salt (e.g., compound B'), or solvate thereof, can be about 0.1:1 or more. In embodiments, the base can be added to the solution in step (a) over a period of time or the base can be added to the solution in step (a) all at once. In some embodiments, the mixture of step (a) can be stirred for about 1 second to about 12 hours. In embodiments, step (a) can occur at a temperature in a range of about 0° C. to about 40° C.

In some embodiments, the first step of the batch process disclosed herein (step (a)) includes admixing (i) a non-nucleophilic base; and (ii) a solution comprising compound B, a salt (e.g., compound B'), or solvate thereof; an ether solvent; and water. In some embodiments, the molar ratio of the base to compound B, a salt (e.g., compound B'), or solvate thereof, is in a range of about 2:1 to about 4:1. In embodiments, the molar ratio of water to compound B, a salt (compound B'), or solvate thereof, can be about 1:1 to about 3:1. In embodiments, the base can be added to the solution in step (a) over a period of time of about 5 seconds to about 6 hours or the base can be added to the solution in step (a) all at once, such as within about 5 seconds. In some embodiments, the mixture of step (a) can be stirred for about 1 second to about 1 hour. In embodiments, step (a) can occur at a temperature in a range of about 15° C. to about 35° C.

In some embodiments, the first step of the methylation process disclosed herein (step (a)) includes admixing (i) potassium HMDS; and (ii) a solution comprising compound B, a salt (e.g., compound B'), or solvate thereof; THF; and water. In some embodiments, the molar ratio of the base to compound B, a salt (e.g., compound B'), or solvate thereof, is in a range of about 3.2:1. In embodiments, the molar ratio of water to compound B, salt (compound B'), or solvate thereof, can be about 1.5:1. In embodiments, the base can be added to the solution in step (a) all at once, such as within about 5 seconds. In some embodiments, the mixture of step (a) can be stirred for about 1 second to about 1 minute. In embodiments, step (a) can occur at room temperature.

In some embodiments, the second step of the methylation process disclosed herein (step (b)) includes admixing the mixture of step (a) and MeX to form a mixture comprising compound A, wherein X is a halogen. In embodiments, the molar ratio of MeX to compound B, salt (e.g., compound B'), or solvate thereof, is in a range of about 1:1 to about 4:1. In some embodiments, the MeX can be admixed with the mixture of step (a) over a time period of about 5 second to about 6 hours or all at once. In embodiments, the mixture of step (b) can be stirred for about 1 second to about 12 hours. In embodiments, step (b) can occur at a temperature in a range of about 0° C. to about 40° C.

In some embodiments, the second step of the methylation process disclosed herein (step (b)) includes admixing the mixture of step (a) and MeX to form a mixture comprising compound A, wherein X is a CI, Br, or I. In embodiments, the molar ratio of MeX to compound B, salt (e.g., compound B'), or solvate thereof, is in a range of about 2:1 to about 4:1. In some embodiments, the MeX can be admixed with the mixture of step (a) over a time period of about 5 second to about 1 hour or all at once. In embodiments, the mixture of step (b) can be stirred for about 1 minute to about 1 hour. In embodiments, step (b) can occur at a temperature in a range of about 15° C. to about 35° C.

In some embodiments, the second step of the methylation process disclosed herein (step (b)) includes admixing the mixture of step (a) and MeI to form a mixture comprising compound A. In embodiments, the molar ratio of MeI to compound B is in a range of about 2.7:1. In some embodiments, the MeI can be admixed with the mixture of step (a) all at once, such as within about 5 seconds. In embodiments, the mixture of step (b) can be stirred for about 5 minutes. In embodiments, step (b) can occur at a temperature at about 20° C.

Flow Chemistry

In some embodiments, the methylation of compound B, a salt (e.g., compound B'), or solvate thereof to form compound A can be accomplished via flow chemistry. Flow chemistry allows for rapid mixing and residence times, as well as a small footprint and efficient throughput during production. Flow chemistry can be advantageous for the process of synthesizing compound A as there is a narrow kinetic window available to produce compound A within drug substance specifications. The flow chemistry can also advantageously provide precise reagent stoichiometry in the process for synthesizing compound A. The rapid mixing times allow compound B, a salt (e.g., compound B'), or solvate thereof, and the base deprotonation reaction (step (a)) to be performed quickly, on the order of seconds, so that compound B, salt (e.g., compound B;), or solvate thereof is not aged with base for a long period of time. Compound B, salt (e.g., compound B'), or solvate thereof, and the base stoichiometry can be adjusted via the flow rate of each reagent, which is another advantageous aspect of the flow chemistry. This rapid residence time provides the contact time and stoichiometry necessary for deprotonation, while preventing the lower conversion obtained from long aging times with a strong base, such as KHMDS.

In some embodiments, the methylation of compound B, a salt (e.g., compound B'), or solvate thereof to form compound A via flow chemistry can comprise a plug flow reactor, a continuous stirred tank reactor, or any combination thereof. In embodiments, the methylation of compound B, a salt (e.g., compound B'), or solvate thereof to form compound A via flow chemistry can comprise multiple continuous stirred tank reactors.

For example, Example 3 describes a flow chemistry process for the methylation of compound B, a salt (e.g., compound B'), or solvate thereof to form compound A. FIG. 1 is a diagram of that flow chemistry process. FIG. 1 shows a diagram of a solution of compound B' and water in a organic solvent along with a solution of KHMDS being added to a plug flow reactor, the plug flow reactor then charges a continuous stirred tank reactor with the activated solution, followed by the addition of Mel to the continuous stirred tank reactor to form a solution comprising compound A, and the solution of compound A is flowed to a collection and diethylamine quench tank.

Figure 2:
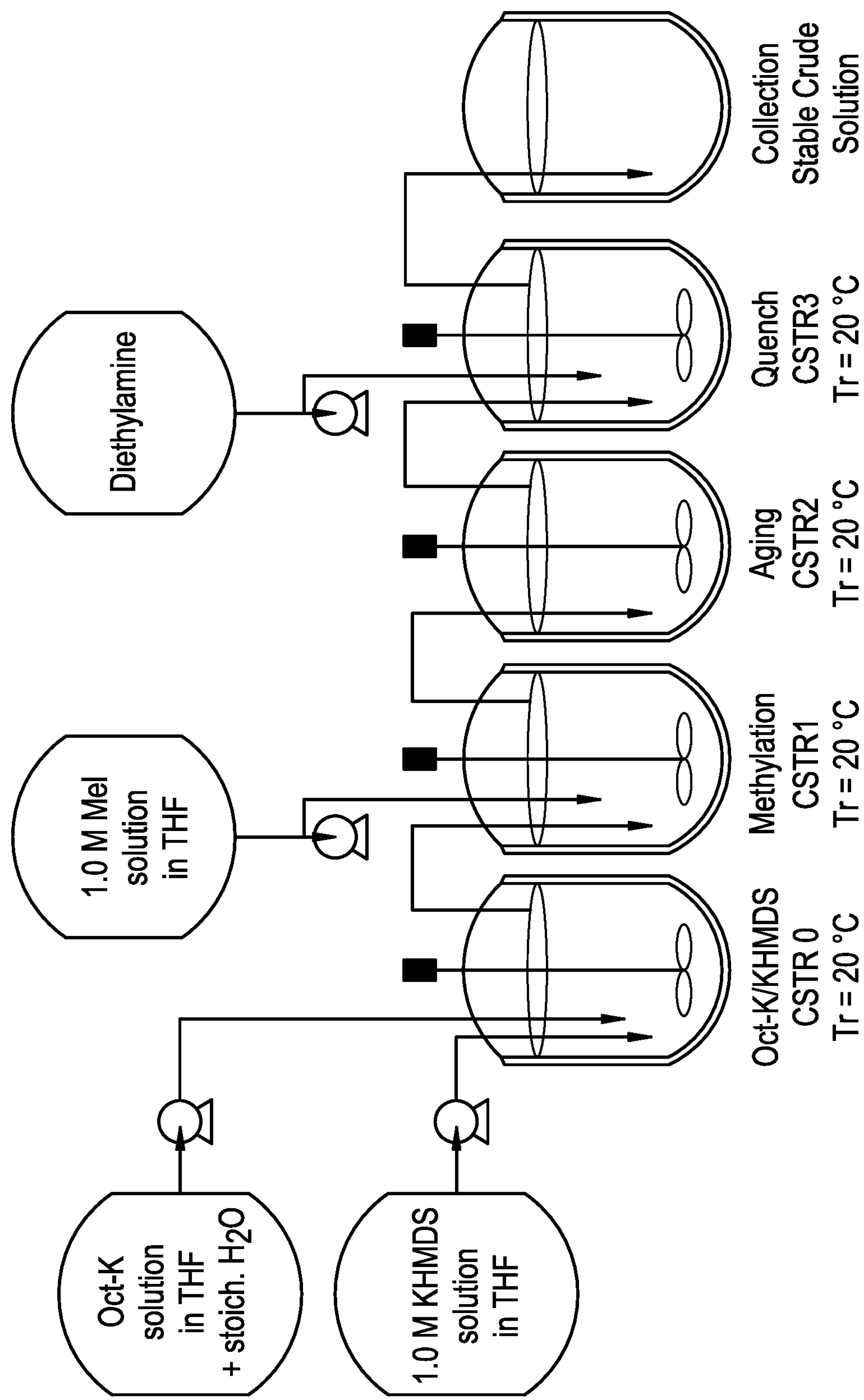
FIG. 2 depicts a diagram of an example flow chemistry process with a flow skid modification, where compound B' (Oct-K) in THF with water and potassium hexamethyldisilazide (KHMDS) are mixed in CSTR 0 (residence time: 5 min), subsequent methylation in CSTR 1 (residence time: 5 min), additional aging in CSTR 2 (residence time: 5 min), and quench with diethylamine in CSTR 3 (residence time: 5 min), as disclosed herein.

As another example, Example 4, describes a flow chemistry process for the methylation of compound B, a salt (e.g., compound B'), or solvate thereof to form compound A, and FIG. 2 is a diagram of that flow chemistry process. FIG. 2 shows a diagram of a solution of compound B' and water in organic solvent along with a solution of KHMDS being added to a continuous stirred tank reactor (CSTR 0). This solution is flowed to another continuous stirred tank reactor (CSTR 1) simultaneously with the addition of a solution of Mel. The solution of CSTR 1 is then flowed to an aging continuous stirred tank reactor (CSTR 2), and the solution in CSTR 2 is flowed to a quenching continuous stirred tank reactor (CSTR 3) where the solution is quenched with diethylamine. The quenched solution from CSTR 3 is flowed to a collection tank as a stable solution comprising compound A.

In the flow chemistry process, compound A can be prepared from compound B, salt (e.g. compound B;), or solvate thereof, in multiple steps. In the first step (step (a)), a base is admixed with a solution comprising compound B, a salt (e.g., compound B'), or solvate thereof; an organic solvent comprising an ether solvent, a nonpolar solvent, or any combination thereof; and water; to form a mixture, optionally in a plug flow reactor. In the second step (step (b)), the mixture of step (a) and methyl halide (MeX) are admixed, optionally in a continuous stirred tank reactor, to form a mixture comprising compound A.

In some embodiments, the first step of the flow chemistry process disclosed herein (step (a)) includes admixing (i) a base selected from the group consisting of a non-nucleophilic base, an alkali metal hydride base, an alkali metal hydroxide base, an organolithium base, and any combination thereof; and (ii) a solution comprising compound B, a salt (e.g., compound B'), or solvate thereof; an organic solvent comprising an ether solvent, a nonpolar solvent, or any combination thereof; and water, in a reactor, such as a plug flow reactor or a continuous stirred tank reactor. In some embodiments, the molar ratio of the base to compound B, a salt (e.g., compound B'), or solvate thereof, is in a range of about 1:1 to about 5:1. In embodiments, the molar ratio of water to compound B, salt (compound B'), or solvate thereof, can be about 0.1:1 or more. In embodiments, the base can be added to the solution in step (a) over a period of time or the base can be added to the solution in step (a) all at once. In some embodiments, the mixture of step (a) can be stirred for about 1 second to about 12 hours. In embodiments, step (a) can occur at a temperature in a range of about 0° C. to about 40° C.

In some embodiments, the first step of the flow chemistry process disclosed herein (step (a)) includes admixing (i) a non-nucleophilic base; and (ii) a solution comprising compound B, a salt, or solvate thereof; an ether solvent; and water, in a plug flow reactor or a continuous stirred tank reactor. In some embodiments, the molar ratio of the base to compound B, a salt (e.g., compound B'), or solvate thereof, is in a range of about 2:1 to about 4:1. In embodiments, the molar ratio of water to compound B can be about 1:1 to about 3:1. In embodiments, the base can be added to the solution in step (a) all at once, such as within about 5 seconds. In some embodiments, the mixture of step (a) can be stirred for about 1 second to about 1 hour. In embodiments, step (a) can occur at a temperature in a range of about 15° C. to about 35° C.

In some embodiments, the first step of the flow chemistry process disclosed herein (step (a)) includes pumping (i) potassium HMDS; and (ii) a solution comprising compound B'; THF; and water into a plug flow reactor with a residence time of about 5 to about 25 seconds. In some embodiments, the molar ratio of the base to compound B, a salt (e.g., compound B'), or solvate thereof is about 3.2:1. In embodiments, the molar ratio of water to compound B can be about 1.5:1. In embodiments, the base can be added to the solution in step (a) all at once, such as within about 5 seconds. In some embodiments, the mixture of step (a) optionally can reside in the plug flow reactor for about 1 second to about 1 minute. In embodiments, step (a) can occur at room temperature, such as 20° C.

In some embodiments, the first step of the flow chemistry process disclosed herein (step (a)) includes admixing (i) potassium HMDS; and (ii) a solution comprising compound B'; THF; and water into a continuous stirred tank reactor. In some embodiments, the molar ratio of the base to compound B, a salt (e.g., compound B'), or solvate thereof, is in a range of about 3.2:1. In embodiments, the molar ratio of water to compound B can be about 1.5:1. In embodiments, the base can be added to the solution in step (a) all at once, such as within about 5 seconds. In some embodiments, the mixture of step (a) can be stirred for about 5 minutes and then transferred to a second continuous stirred tank reactor. In embodiments, step (a) can occur at room temperature.

In some embodiments, the second step of the flow chemistry process disclosed herein (step (b)) includes admixing the mixture of step (a) and MeX in a reactor, such as a continuous stirred reactor tank, to form a mixture comprising compound A, wherein X is a halogen. In some embodiments, the mixture comprising compound A can be transferred to one or more reactor tanks, such as continuous stirred reactor tanks. In embodiments, the molar ratio of MeX to compound B is in a range of about 1:1 to about 10:1. In some embodiments, the MeX can be admixed with the mixture of step (a) over a time period of about 1 second to about 6 hours or all at once. In embodiments, the mixture of step (b) can be stirred for about 1 second to about 12 hours. In embodiments, step (b) can occur at a temperature in a range of about 0° C. to about 40° C.

In some embodiments, the second step of the flow chemistry process disclosed herein (step (b)) includes admixing the mixture of step (a) and MeX in a reactor, such as a continuous stirred reactor tank, to form a mixture comprising compound A, wherein X is a CI, Br, or I. In some embodiments, the mixture comprising compound A is transferred to one or more reactor tanks, such as continuous stirred reactor tanks. In embodiments, the molar ratio of MeX to compound B is in a range of about 2:1 to about 4:1. In some embodiments, the MeX can be admixed with the mixture of step (a) over a time period of about 1 second to about 1 hour or all at once. In embodiments, the mixture of step (b) can be stirred for about 1 minute to about 1 hour. In embodiments, step (b) can occur at a temperature in a range of about 15° C. to about 35° C.

In some embodiments, the second step of the flow chemistry process disclosed herein (step (b)) includes admixing the mixture of step (a) and MeX in a continuous stirred reactor tank, to form a mixture comprising compound A, wherein X is an iodide and, the mixture comprising compound A is transferred to a second continuous stirred reactor tank. In embodiments, the molar ratio of MeX to compound B is in a range of about 2.7:1. In some embodiments, the MeX can be admixed with the mixture of step (a) all at once, such as within about 5 seconds. In embodiments, the mixture of step (b) can be stirred for about 5 minutes and then transferred to a second continuous stirred reactor tank and again, stirred for about 5 minutes. In embodiments, step (b) can occur at a temperature at about 20° C.

In embodiments, the flow chemistry process for the methylation of compound B can have a third step. In the third step, the mixture of step (b) can be further added to a reactor, such as a continuous stirred tank reactor, and quenched with a base (e.g., a secondary amine base). In embodiments, the mixture of the third step can be stirred for about 1 minute to about 48 hours. In embodiments, step (b) can occur at a temperature in a range of about 0° C. to about 40° C. In some embodiments, the third step includes the mixture of step (b) being transferred to a new reactor, such as a continuous stirred tank reactor and quenched with a secondary amine base. In embodiments, the mixture of the third step can be stirred for 1 minute to about 1 hour. In embodiments, step (b) can occur at a temperature in a range of about 15° C. to about 35° C. In some embodiments, the third step includes the mixture of step (b) being transferred to a continuous stirred reactor and quenched with diethylamine. In embodiments, the mixture of the third step can be stirred for about 5 minutes. In embodiments, step (b) can occur at a temperature in a range of about 20° C., or room temperature.

Preparation of Compound B'

Compound A can be prepared by methylating a salt form of compound B, such as compound B'. In certain embodiments, it can be advantageous to synthesize compound A from a salt form of compound B, such as compound B'. In some embodiments, compound B, which is a free acid, can have low solubility in certain solvents, which can provide a challenge for reaction reproducibility. Compound B' can provide improved reproducibility and consistency because it is more easily solubilized in the certain solvents. Compound B' can be prepared by admixing compound B with a base and an organic solvent to form a mixture comprising compound B'. In embodiments, the base can be an alkali hydroxide base. In embodiments, the organic solvent can be selected from the group consisting of an ether solvent, a nonpolar solvent, and any combination thereof.

In embodiments, the alkali hydroxide base can be selected from the group consisting of potassium hydroxide, sodium hydroxide, lithium hydroxide, and any combination thereof. In some embodiments, the alkali hydroxide base is potassium hydroxide. In embodiments, the molar ratio of the alkali hydroxide base to compound B is in a range of about 0.5:1 to about 10:1, or about 0.5:1 to about 5:1, or about 0.5:1 to about 3:1, or about 0.5:1 to about 2:1, or about 1:1 to about 3:1, or about 1:1 to about 2:1. In embodiments, the molar ratio of the alkali hydroxide base to compound B is about 0.5:1, about 1:1, about 1.5:1, about 2:1, about 2.5:1, about 3:1, about 4:1, about 5:1, about 6:1, about 7:1, about 8:1, about 9:1, or about 10:1. In embodiments, the molar ratio of the alkali hydroxide base to compound B is about 1.5:1.

In embodiments, the organic solvent can be selected from the group consisting of an ether solvent, a nonpolar solvent, and any combination thereof. In some cases, the organic solvent can be an ether solvent. Suitable ether solvents can include, for example, tetrahydrofuran (THF), 2-methyltetrahydrofuran (MeTHF), cyclopentyl methyl ether, tert-butyl methyl ether, 1,2-dimethoxyethane, 1,4-dioxane, diethyl ether, diisopropyl ether, bis(2-methoxyethyl) ether, propylene glycol methyl ether, and any combination thereof. In embodiments, the ether solvent can be THF or 2-methyltetrahydrofuran. In some cases, the organic solvent can be a nonpolar solvent. Suitable nonpolar solvents can include, for example, hexane, pentane, toluene, benzene, heptane, xylene, and any combination thereof. In embodiments, the nonpolar solvent can be toluene, hexane, heptane, or any combination thereof. In embodiments, the organic solvent can be selected from the group consisting of THF, 2-methyltetrahydrofuran, cyclopentyl methyl ether, tert-butyl methyl ether, 1,2-dimethoxyethane, toluene, hexane, heptane, 1,4-dioxane, and any combination thereof. In some embodiments, the organic solvent is THF.

In embodiments, the mixture comprising compound B' can be stirred for about 1 hour to about 48 hours, or about 2 hours to about 6 hours, or about 2 hours to about 10 hours, or about 5 hours to about 10 hours, or about 6 hours to about 12 hours, or about 12 hours to 24 hours, or about 15 hours to about 24 hours, or about 10 hours to about 20 hours, or about 24 hours to 48 hours, or about 30 hours to 40 hours, or about 30 hours to about 48 hours, or about 40 hours to about 48 hours. In some embodiments, the mixture comprising compound B' can be stirred for about 1 hour, about 2 hours, about 3 hours, about 4 hours, about 5 hours, about 6 hours, about 7 hours, about 8 hours, about 9 hours, about 10 hours, about 11 hours, or about 12 hours, about 15 hours, about 20 hours, about 24 hours, about 30 hours, about 35 hours, about 40 hours, about 48 hours.

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims. For example, as shown in Examples 1-6.

EXAMPLES

The following examples are provided for illustration and are not intended to limit the scope of the invention.

Materials and Methods

Commercially available reagents are used as is without further purification unless specified. The 1.0 M Mel in THF solution is prepared by weight. The batch and flow chemistry equipment (reactors, tubing, pumps, connections and fittings) is from commercially available sources.

The synthesis of the starting material (compound B) for the following synthetic methods is disclosed in U.S. Pat. No. 10,300,075. The starting materials, the intermediates, and final products of the reactions may be isolated and purified, if desired, using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure and a temperature in a range of about −78° C. to about 150° C., or about 0° C. to about 50° C., or about 15° C. to about 25° C.

Example 1: Preparation of Compound B' from Compound B

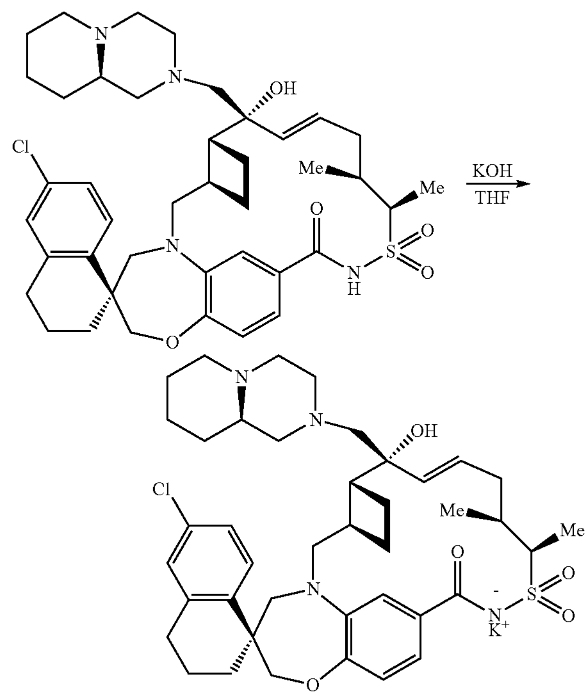

((4S,7aR,9aR,10R,11E,14S,15R)-6'-chloro-10-hydroxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H,17H)-trione potassium salt (Compound B'): To a round bottom flask containing solid potassium hydroxide (28 g, 0.43 mol, 1.5 equiv.), compound B (214 g, 0.285 mol, 1.0 equiv.) was added, followed by anhydrous tetrahydrofuran (2.8 L, 0.10 M). The solution was stirred at 20° C. for at least 12 hours. The solution was then filtered, rinsed with tetrahydrofuran (211 mL), and the filtrates were combined. The filtrate was azeotropically dried by distillation to yield a solution at 0.090-0.10 M in THF, containing 1.4-1.6 equiv. of water. The compound B' solution was then used directly in the next step. $^1$H NMR (600 MHz, THF-$d_8$): δ 7.726 (d, J=8.4 Hz, 1H), 7.314 (br s, 1H), 7.181 (br d, J=7.5 Hz, 1H), 7.074 (dd, J=8.4, 2.0 Hz, 1H), 7.010 (d, J=2.0 Hz, 1H), 6.569 (br d, J=7.5 Hz, 1H), 6.080 (m, 1H), 5.705 (br d, J=15.4 Hz, 1H), 4.032 (br d, J=13.6 Hz, 1H), 3.893 (m, 2H), 3.662 (m, 1H) 3.639 (m, 1H), 3.317 (br d, J=14.1 Hz, 1H), 2.976 (m, 1H), 2.957 (m, 1H), 2.741 (m, 1H), 2.709 (m, 1H), 2.679 (m, 1H), 2.641 (br d, J=10.5 Hz, 1H), 2.455 (br d, J=9.9 Hz, 1H), 2.433 (m, 1H), 2.419 (m, 1H), 2.307 (m, 1H), 2.242 (m, 1H), 2.193 (m, 1H), 2.178 (m, 2H), 2.121 (m, 1H), 2.055 (m, 1H), 1.956 (m, 1H), 1.929 (m, 1H), 1.877 (m, 1H), 1.868 (m, 2H), 1.859 (m, 1H), 1.811 (m, 1H), 1.652 (m, 1H), 1.639 (m, 1H), 1.630 (m, 1H), 1.520 (m, 1H), 1.482 (m, 2H), 1.340 (m, 1H), 1.299 (m, 1H), 1.239 (br d, J=7.0 Hz, 3H), 1.197 (m, 1H), 1.076 (m, 1H), 0.948 (br d, J=6.6 Hz, 3H); $^{13}$C NMR (151 MHz, THF-$d_8$): δ 175.4, 151.4, 141.7, 140.6, 140.0, 135.8, 134.2, 132.6, 131.0, 129.9, 129.2, 127.4, 120.5, 120.3, 116.3, 81.1, 76.3, 67.1, 63.2, 62.3, 61.3, 60.9, 56.9, 56.5, 56.3, 49.5, 43.6, 38.9, 35.8, 34.6, 31.2, 30.9, 29.3, 27.5, 27.0, 25.3, 22.4, 20.3, 17.1, 8.1.

Example 2: Batch Preparation of Compound A from Compound B'

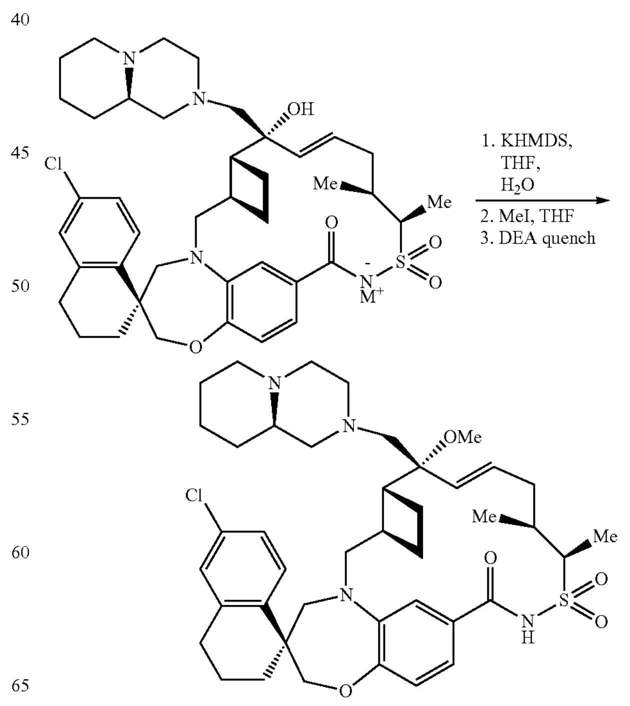

The compound B' in THF solution containing 1.5 equiv. water is prepared from compound B according to Example 1.

To a solution of compound B' (100 mg, 0.1 mmol, 1.0 equiv. containing 1.5±0.1 equiv. water) in THF (1.3 mL, 13 vol.), anhydrous THF (1.2 mL, 12 vol.) was added. 1.0 M KHMDS in THF (0.32 mL, 0.32 mmol, 3.2 equiv.) was then rapidly charged to the stirring compound B' solution all at once within 15 sec. Immediately after the KHMDS solution was charged, a solution of 1.0 M MeI in THF (0.27 mL, 0.27 mmol, 2.7 equiv.) was then rapidly charged to the stirring reaction mixture all at once within 15 sec. After stirring for 5 min, the reaction was quenched with diethylamine (0.16 mL, 1.5 mmol, 15.0 equiv.).

Example 3: Flow Chemistry Procedure 1—Plug Flow Reactor and Continuous Stirred-Tank Reactor Methylation Reaction Flow Process (4S,7aR,9aR,10R,11E,14S,15R)-6'-chloro-10-methoxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H,17H)-trione (Compound A): The compound B' in THF solution (1.0 equiv., 80 g/min), 1.0 M KHMDS in THF solution (3.2 equiv.), and anhydrous THF (1.4 L) were pumped into the Plug Flow Reactor (PFR) with a residence time of 15 seconds at 20° C. The compound B' in THF solution containing 1.5 equiv. water was prepared from compound B according to Example 1. The PFR eluent and a 1.0 M the iodomethane in THF solution (2.7 equiv.) were simultaneously added to Continuous Stirred-Tank Reactor 1 (CSTR 1). The reaction slurry was aged for 5 min at 20° C. in CSTR 1, then transferred to a second reactor (CSTR 2). The slurry was aged in CSTR 2 for 5 min at 20° C. The resulting slurry was transferred from CSTR 2 to CSTR 3. In CSTR 3, N,N-diethylamine (15 equiv.) was simultaneously added. The slurry was aged in CSTR 3 for 5 min at 20° C. The crude stream was collected in fractions from CSTR 3 for analysis. The collected fractions that contained the crude stream at >95% conversion were taken forward through the isolation process. FIG. 1 shows an example flow process diagram of this process.

Example 4: Flow Chemistry Procedure 2—4 x Continuous Stirred-Tank Reactor Methylation Reaction Flow Process (4S,7aR,9aR,10R,11E,14S,15R)-6'-chloro-10-methoxy-14,15-dimethyl-10-{[(9aR)-octahydro-2H-pyrido[1,2-a]pyrazin-2-yl]methyl}-3',4',7a,8,9,9a,10,13,14,15-decahydro-2'H,3H,5H-spiro[1,19-etheno-16I6-cyclobuta[i][1,4]oxazepino[3,4-f][1,2,7]thiadiazacyclohexadecine-4,1'-naphthalene]-16,16,18(7H,17H)-trione (Compound A): The compound B' in THF solution (116 g, 0.15 mol, 1.0 equiv.) was diluted with anhydrous THF (1.4 L). The compound B' in THF solution containing 1.5 equiv. water is prepared from compound B according to Example 1. The compound B' in THF (1.0 equiv., 16.7 mL/min) and 1.0 M KHMDS in THF (3.2 equiv.) solutions were simultaneously added to CSTR 0. The resulting solution was aged for 5 minutes at 20° C. in CSTR 0, then transferred to CSTR 1. The 1.0 M iodomethane in THF solution (2.7 equiv.) was simultaneously added to CSTR 1. The reaction slurry was aged for 5 min at 20° C. in CSTR 1, then transferred from CSTR 1 to CSTR 2. The slurry was aged in CSTR 2 for 5 min at 20° C., then transferred from CSTR 2 to CSTR 3. In CSTR 3, N,N-diethylamine (15 equiv.) was simultaneously added. The slurry was aged in CSTR 3 for 5 min at 20° C. The crude stream was collected in fractions from CSTR 3 for analysis. The collected fractions that contained the crude stream at >95% conversion were taken forward through the isolation process. FIG. 2 shows an example process flow diagram of this process.

Example 5: General Isolation Process (e.g., for Example 2, Example 3, and Example 4)

Compound A was isolated from the crude solution of Example, 2, Example 3, and Example 4 as follows. The crude solution was filtered at 20° C. The solution was then concentrated to about 0.13 M at 40° C. under vacuum. The concentrated solution was polish filtered. To the filtered solution, 5 N NaOH (51 mL) was charged, followed by a 13 wt % NaCl solution (206 mL). The solution was agitated for at least 5 min at 20° C. The agitation was stopped, and the phases were allowed to separate for at least 5 min at 20° C. The aqueous layer was removed. A 13 wt % NaCl solution (206 mL) was charged to the organic layer, and the batch was agitated for at least 5 min at 20° C. The agitation was stopped, and the phases were allowed to separate for at least 5 min at 20° C. The aqueous layer was removed. Denatured ethanol with 2% v/v toluene (946 mL) was charged to the organic layer. The batch was distilled to about 0.13 M at 50° C. under vacuum. Denatured ethanol with 2% v/v toluene (997 mL) was charged to the distilled solution, and the batch was distilled to about 0.13 M at 50° C. under vacuum. Another charge of denatured ethanol with 2% v/v toluene (997 mL) was charged to the distilled solution, and the distillation was repeated once more. The batch was polish filtered and then heated to 80±5° C. After reaching temperature, 3 N AcOH (22 mL, 0.14 mol, 0.5 eq) was charged to the heated solution. The solution was aged at 80±5° C. for at least 15 min. In a separate vessel, a slurry of Compound A seed (0.51 g) in denatured ethanol with 2% v/v toluene (2.6 mL) was prepared. The seed slurry was then charged to the heated solution. The solution was aged for at least 15 mins at 80° C.±5° C. A solution of 3N AcOH (108 mL, 0.70 mol, 2.5 eq.) was then charged over a period of 1 h at 80° C. Then, the batch was slowly cooled to 20° C. over a period of 1 h. The slurry was aged at 20° C. for at least an additional 1 h, followed by filtration of the solid. The cake was washed with denatured ethanol with 2% v/v toluene (2×308 mL). The filtered solids were dried at 65° C. under vacuum for at least 12 h to obtain compound A (75.6 g, 96.1 wt %, 76% yield): IR (thin film, $cm^{-1}$): 2936.63, 1507.87, 1341.57, 1308.78, 1257.25, 1212.75, 1184.65, 1095.64, 1008.98, 812.23, 777.10, 568.64; $^1H$ NMR (600.13 MHz, DMSO-$d_6$): δ 7.671 (d, J=8.5 Hz, 1H), 7.241 (dd, J=8.5, 2.4 Hz, 1H), 7.190 (br d, J=1.9 Hz, 1H), 7.153 (d, J=2.4 Hz, 1H), 7.018 (dd, J=8.1, 1.9 Hz, 1H), 6.825 (d, J=8.1 Hz, 1H), 5.633 (dt, J=16.2, 5.5 Hz, 1H), 5.430 (br d, J=16.2 Hz, 1H), 4.031 (d, J=12.3 Hz, 1H), 3.981 (d, J=12.3 Hz, 1H), 3.874 (br d, J=15.0 Hz, 1H), 3.810 (q, J=6.5 Hz, 1H), 3.579 (d, J=14.2 Hz, 1H), 3.254 (s, 3H), 3.212 (d, J=14.2 Hz, 1H), 3.019 (br d, J=10.7 Hz, 1H), 2.953 (br dd, J=15.0, 10.4 Hz, 1H), 2.907 (m, 1H), 2.796 (m, 1H), 2.793 (m, 1H), 2.717 (m, 1H), 2.610 (m, 1H), 2.580 (m, 1H), 2.489 (m, 1H), 2.447 (br d, J=14.2 Hz, 1H), 2.431 (m, 1H), 2.303 (m, 1H), 2.300 (m, 1H), 2.268 (br d, J=14.2 Hz, 1H), 2.253 (m, 1H), 2.219 (m, 1H), 2.202 (m, 1H), 2.059 (m, 1H), 2.031 (m, 1H), 2.001 (m, 1H), 1.858 (m, 2H), 1.781 (m, 1H), 1.688 (br d, J=15.3 Hz, 1H), 1.654 (m, 1H), 1.634 (m, 1H), 1.612 (m, 1H), 1.524 (m, 1H), 1.519

(m, 1H), 1.445 (m, 1H), 1.403 (m, 1H), 1.303 (m, 1H), 1.227 (d, J=7.1 Hz, 3H), 1.191 (m, 1H), 0.945 (d, J=6.7 Hz, 3H); $^{13}C$ NMR (150.90 MHz, DMSO-$d_6$): δ 169.0, 150.5, 139.8, 139.1, 130.6, 130.2, 129.3, 128.7, 127.9, 126.0, 119.0, 117.2, 115.4, 80.9, 79.5, 60.8, 59.9, 59.6, 58.9, 57.9, 55.7, 54.0, 53.7, 52.4, 49.8, 43.8, 41.3, 35.8, 32.0, 31.5, 29.3, 28.1, 27.7, 26.1, 24.2, 22.6, 21.2, 18.3, 15.0, 5.9; HRMS (ESI): Calcd. for C42H57ClN4O5S+H 765.38, found: 765.38.

Example 6—Stoichiometric Addition of Water

The process of Example 2 was followed except that the amount of water used was changed in each of the three reactions as well as the amount of base. A range of equivalents of water (0.6-3.0 eq) were tested to establish the the amount of water tolerated in the reaction and the amount necessary for the reaction to proceed with >98% conversion (Table 1). As long as the equivalents of base were adjusted to compensate for the increase in equivalents of water, the reaction proceeded with >97% conversion. Using greater than 1.0 eq water provided >99% conversion and <0.05% dimethyl impurity. Without water, inconsistencies were observed in conversion to compound A over replicate trials.

TABLE 1

| Experiment | Water Eq | KHMDS Eq | MeI Eq | % Conversion to Compound A |
|---|---|---|---|---|
| 1 | 0.64 | 3.4 | 2.5 | 95.5 |
| 2 | 1.5 | 4.0 | 2.5 | 98.4 |
| 3 | 3 | 5.5 | 2.5 | 99.3 |

Example 7— Rapid Addition of the KHMDS to Compound B', Followed by Immediate Addition of MeI The rate of addition of both KHMDS and MeI were tested to determine if the addition rate of either component plays a role in the reaction efficiency (Table 2). It was found that a more effective reaction occurred when the addition of KHMDS was rapid (within seconds). If KHMDS was added to compound B' over 20 minutes, a decrease in conversion was observed. The addition rate of MeI did not appear to affect the reaction conversion.

TABLE 2

| Experiment | Water Eq | KHMDS Eq | MeI Eq | Rate of Addition | % Conversion to Compound A |
|---|---|---|---|---|---|
| 1 | 3 | 5.5 | 2.5 | Control - rapid addition | 98.5% |
| 2 | 3 | 5.5 | 2.5 | MeI over 20 minutes | 98.8% |
| 3 | 3 | 5.5 | 2.5 | KHMDS over 20 minutes | 89.9% |

Example 8: Preparation and Characterization of Crystalline Hydrate Form of Compound A The crystalline hydrate form of compound A was formed by combining compound A with ~10 volumes of 95:5 ethanol/water. Heat cycled to 70° C. in sealed vial for 15 min then cooled.

X-Ray Powder Diffraction: X-ray powder diffraction data were obtained on a PANalytical X'Pert PRO X-ray diffraction system with RTMS detector. Samples were scanned in continuous mode from 5-45° (2θ) with step size of 0.0334° at 45 kV and 40 mA with CuKα radiation (1.54 Å). The incident beam path was equipped with a 0.02 rad soller slit, 15 mm mask, 4° fixed anti-scatter slit and a programmable divergence slit. The diffracted beam was equipped with a 0.02 rad soller slit, programmable anti-scatter slit and a 0.02 mm nickel filter. Samples were prepared on a low background sample holder and placed on a spinning stage with a rotation time of 2 s. For variable-temperature studies, samples were prepared on a flat plate sample holder and placed in a TTK-450 temperature control stage. For variable-humidity studies, modular humidity generator generator (ProUmid) was used to control atmosphere in THC humidity sample chamber. The XRPD pattern of the crystalline hydrate form of compound A material is shown in FIG. 7 and the XRPD peaks are listed in Table 3.

Thermal Analysis: Differential scanning calorimetry (DSC) was performed on a TA Instruments Q1000/2000 calorimeter at in an aluminum Tzero pan under dry nitrogen, flowing at 50 ml/min. The DSC of the crystalline hydrate form of compound A is shown in FIG. 4. Thermogravimetric analysis (TGA) was performed on a TA Instruments Q500 analyzer in a platinum pan under dry nitrogen, flowing at 60 ml/min. The DSC and TGA of the crystalline hydrate form of compound A is shown in FIGS. 4 and 5.

Moisture Sorption: Moisture sorption data was collected using a Surface Measurement Systems DVSAdvantage instrument. Equilibrium criteria were set at ±0.001% weight change in 10 minutes with a maximum equilibrium time of 360 minutes. The moisture sorption profile of the crystalline hydrate form of compound A is shown in FIG. 6.

TABLE 3

XRPD Data Table

| Pos. [°2θ] | FWHM [°2θ] | d-spacing [Å] | Height [cts] | Rel. Int. [%] |
|---|---|---|---|---|
| 8.08 | 0.13 | 10.95 | 8694.81 | 13.74 |
| 10.28 | 0.13 | 8.60 | 40462.38 | 63.92 |
| 10.72 | 0.13 | 8.25 | 15279.74 | 24.14 |
| 11.98 | 0.15 | 7.39 | 9563.74 | 15.11 |
| 12.48 | 0.15 | 7.10 | 14996.68 | 23.69 |
| 13.25 | 0.18 | 6.68 | 13655.34 | 21.57 |
| 14.38 | 0.15 | 6.16 | 10404.72 | 16.44 |
| 14.69 | 0.15 | 6.03 | 11131.10 | 17.58 |
| 15.11 | 0.20 | 5.87 | 23166.31 | 36.60 |
| 15.90 | 0.13 | 5.58 | 6572.05 | 10.38 |
| 16.30 | 0.20 | 5.44 | 38727.58 | 61.18 |

TABLE 3-continued

| XRPD Data Table | | | | |
|---|---|---|---|---|
| Pos. [°2θ] | FWHM [°2θ] | d-spacing [Å] | Height [cts] | Rel. Int. [%] |
| 17.13 | 0.23 | 5.18 | 63299.61 | 100.00 |
| 17.74 | 0.17 | 5.00 | 15095.93 | 23.85 |
| 18.23 | 0.20 | 4.87 | 14190.89 | 22.42 |
| 19.78 | 0.20 | 4.49 | 11371.71 | 17.96 |
| 20.29 | 0.18 | 4.38 | 28258.72 | 44.64 |
| 20.88 | 0.20 | 4.25 | 11394.74 | 18.00 |
| 21.69 | 0.10 | 4.10 | 7304.56 | 11.54 |
| 21.92 | 0.18 | 4.06 | 9295.19 | 14.68 |
| 25.01 | 0.17 | 3.56 | 8487.99 | 13.41 |
| 25.44 | 0.15 | 3.50 | 8971.11 | 14.17 |
| 25.62 | 0.23 | 3.48 | 7561.08 | 11.94 |

TABLE 4

| Solid State $^{13}C$ NMR Data | | | |
|---|---|---|---|
| Peak | v(F1) [ppm] | Intensity [abs] | Intensity [rel] |
| 1 | 174.30 | 3342800.86 | 5.47 |
| 2 | 151.76 | 4875738.84 | 7.98 |
| 3 | 143.08 | 4937517.05 | 8.08 |
| 4 | 141.47 | 4895517.41 | 8.01 |
| 5 | 139.72 | 5473393.72 | 8.95 |
| 6 | 134.99 | 5045623.66 | 8.25 |
| 7 | 133.87 | 4070943.45 | 6.66 |
| 8 | 133.18 | 6027611.34 | 9.86 |
| 9 | 130.53 | 5629472.55 | 9.21 |
| 10 | 128.11 | 4354315.61 | 7.13 |
| 11 | 124.60 | 2996501.88 | 4.90 |
| 12 | 123.10 | 3691109.91 | 6.04 |
| 13 | 115.91 | 3157834.66 | 5.17 |
| 14 | 85.23 | 6108149.53 | 10.00 |
| 15 | 78.05 | 2851707.20 | 4.67 |
| 16 | 65.65 | 4420846.34 | 7.23 |
| 17 | 61.80 | 2795012.02 | 4.57 |
| 18 | 60.23 | 6067426.56 | 9.93 |
| 19 | 57.78 | 3987290.50 | 6.52 |
| 20 | 57.28 | 4156007.39 | 6.80 |
| 21 | 56.15 | 3763019.48 | 6.16 |
| 22 | 54.40 | 3012506.42 | 4.93 |
| 23 | 51.84 | 4997182.81 | 8.17 |
| 24 | 50.30 | 3249618.88 | 5.32 |
| 25 | 49.53 | 4677813.33 | 7.66 |
| 26 | 43.15 | 5294261.23 | 8.67 |
| 27 | 39.48 | 2715242.14 | 4.44 |
| 28 | 38.27 | 3420418.53 | 5.60 |
| 29 | 36.84 | 3868181.97 | 6.33 |
| 30 | 31.05 | 3434460.58 | 5.62 |
| 31 | 30.09 | 3714100.47 | 6.08 |
| 32 | 27.75 | 2815977.80 | 4.61 |
| 33 | 25.54 | 3625318.16 | 5.93 |
| 34 | 24.04 | 2903757.64 | 4.75 |
| 35 | 20.39 | 2695161.47 | 4.41 |
| 36 | 19.13 | 4118642.73 | 6.74 |
| 37 | 13.57 | 3585801.05 | 5.87 |

Single Crystal Data: A dry powder sample of compound A crystalline hydrate form was used for single crystal structure determination. The specimen chosen for data collection was a needle with the approximate dimensions 0.002×0.008×0.025 $mm^3$. The crystal was mounted on a MiTeGen™ mount with mineral oil (STP Oil Treatment). First diffraction patterns showed the crystal to be of marginal quality giving rise to smeared, elongated and split reflections, and diffracting only weakly.

Diffraction data (φ- and ω-scans) were collected at 100K on a Bruker-AXS X8 Kappa diffractometer coupled to a Bruker APEX2 CCD detector using Cu Kα radiation (λ=1.54178 Å) from an /μS microsource. Data reduction was carried out with the program SAINT[1] and semi-empirical absorption correction based on equivalents was performed with the program SADABS[2]. A summary of crystal properties and data/refinement statistics is given in Table 5.

The structure of compound A crystalline hydrate was determined at 100K in the monoclinic chiral space group P21 with one molecule of compound A and 80% of a water molecule in the asymmetric unit.

TABLE 5

| X-ray Single Structure Data | | |
|---|---|---|
| Wavelength | 1.54178 Å | |
| Crystal system | Monoclinic | |
| Space group | $P2_1$ | |
| Unit cell dimensions | a = 10.9544(10) Å | α = 90° |
| | b = 13.6828(9) Å | β = 92.724(6)° |
| | c = 13.4164(9) Å | γ = 90° |
| Volume | 2008.7(3) $Å^3$ | |
| Z | 2 | |
| Density (calculated) | 1.289 $Mg/m^3$ | |
| Absolute structure parameter | −0.008(18) | |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

The use of the terms "a," "an," "the," and similar referents in the context of the disclosure herein (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure herein and is not a limitation on the scope of the disclosure herein unless otherwise indicated. No language in the specification should be construed as indicating any non-claimed element as essential to the practice of the disclosure herein.

All patents, publications and references cited herein are hereby fully incorporated by reference. In case of conflict between the present disclosure and incorporated patents, publications and references, the present disclosure should control.

We claim:

1. A process for synthesizing compound A, a salt, or a solvate thereof:

(A)

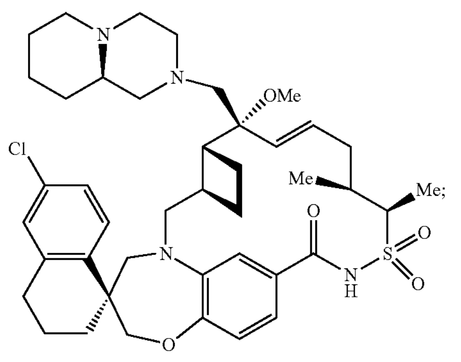

comprising:

(a) admixing:

(i) a base selected from the group consisting of a non-nucleophilic base, an alkali metal hydride base, an alkali metal hydroxide base, an organolithium base, and any combination thereof; and (ii) a solution comprising compound B, a salt, or solvate thereof:

(B)

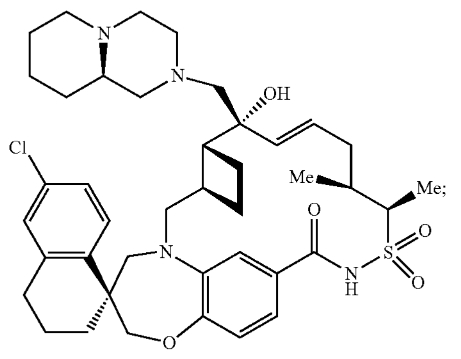

and an organic solvent comprising an ether solvent, a nonpolar solvent, or any combination thereof; and water, wherein the molar ratio of water to compound B is in a range of about 0.5:1 to about 3:1, to form a mixture; and (b) admixing the mixture of step (a) and MeX to form a mixture comprising compound A, wherein X is a halogen.

2. The process of claim 1, wherein the base comprises lithium hexamethyldisilazide ("HMDS"), sodium HMDS, potassium HMDS, lithium diisopropylamide, sodium diisopropylamide, potassium diisopropylamide, lithium tert-butoxide, sodium tert-potassium tert-butoxide, lithium tert-amylate, sodium tert-amylate, potassium tert-butoxide, amylate, potassium hydride, sodium hydride, potassium hydroxide, sodium hydroxide, lithium hydroxide, 2,2,6,6-Tetramethylpiperidine (TMP), LiTMP, n-butyllithium (n-BuLi), n-hexyllithium, 1,1,3,3-tetramethylguanidine (TMG), 1,8-diazabicyclo[5.4.0]undec-7-ene (DBU), 1,5-diazabicyclo[4.3.0]non-5-ene, or any combination thereof.

3. The process of claim 2, wherein the base comprises lithium hexamethyldisilazide HMDS, sodium HMDS, potassium HMDS, or any combination thereof.

4. The process of claim 3, wherein the base comprises potassium hexamethyldisilazide ("KHMDS").

5. The process of claim 1, wherein the molar ratio of the base to compound B is in a range of about 1:1 to about 5:1.

6. The process of claim 5, wherein the molar ratio of the base to compound B is in a range of about 2.5:1 to about 4:1.

7. The process of claim 5, wherein the molar ratio of the base to compound B is about 3.0:1 to about 3.5:1.

8. The process of claim 5, wherein the molar ratio of the base to compound B is about 3.2:1.

9. The process of claim 1, wherein the organic solvent is selected from the group consisting of tetrahydrofuran ("THF"), 2-methyltetrahydrofuran, cyclopentyl methyl ether, tert-butyl methyl ether, 1,2-dimethoxyethane, toluene, hexane, heptane, 1,4-dioxane, and combinations thereof.

10. The process of claim 9, wherein the organic solvent comprises THF.

11. The process of claim 1, wherein the molar ratio of water to compound B is in a range of about 1:1 to about 3:1.

12. The process of claim 1, wherein the molar ratio of water to compound B is about 1.4:1 to about 1.6:1.

13. The process of claim 1, wherein X is iodide.

14. The process of claim 1, wherein the molar ratio of MeX to compound B is in a range of about 1:1 to about 4:1.

15. The process of claim 14, wherein the molar ratio of MeX to compound B is about 2.7:1.

16. The process of claim 1, wherein the base is admixed with the solution in step (a) over a time period of about 5 seconds to about 6 hours.

17. The process of claim 1, wherein the base is admixed with the solution in step (a) within 5 seconds.

18. The process of claim 17, wherein the base is admixed with the solution in step (a) within 1 second.

19. The process of claim 1, wherein the mixture of step (a) is stirred for about 1 second to about 12 hours.

20. The process of claim 19, wherein the mixture of step (a) is stirred for about 1 second to about 20 minutes.

21. The process of claim 1, wherein the MeX is admixed with the mixture of step (a) over a time period of about 1 second to about 6 hours.

22. The process of claim 1, wherein the MeX is admixed with the mixture of step (a) within 5 seconds.

23. The process of claim 22, wherein the MeX is admixed with the mixture of step (a) within 1 second.

24. The process of claim 1, wherein the mixture of step (b) is stirred for about 1 minute to 12 hours.

25. The process of claim 24, wherein the mixture of step (b) is stirred for about 1 minute to about 20 minutes.

26. The process of claim 1, wherein compound B is a solvate prior to preparation of the solution recited in step (ii) of claim 1.

27. The process of claim 1, wherein compound B is a salt prior to preparation of the solution recited in step (ii) of claim 1, having a structure of compound B':

(B')

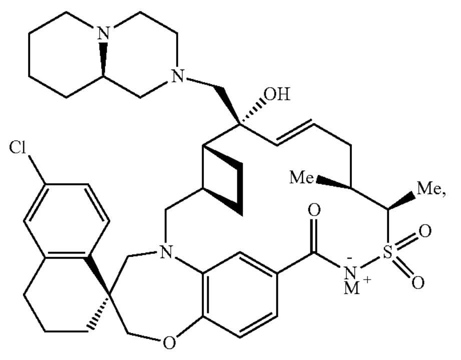

wherein M is an alkali metal.

28. The process of claim 27, wherein the alkali metal is lithium, sodium, or potassium.

29. The process of claim 28, wherein the alkali metal is potassium.

30. The process of claim 27, wherein compound B' is prepared by admixing compound B with an alkali hydroxide base and an organic solvent selected from the group consisting of an ether solvent, a nonpolar solvent, and any combination thereof, to form a mixture comprising compound B'.

31. The process of claim 30, wherein the alkali hydroxide base is selected from the group consisting of potassium hydroxide, sodium hydroxide, lithium hydroxide, and combinations thereof.

32. The process of claim 30, wherein the molar ratio of the alkali hydroxide base to compound B is in a range of about 0.5:1 to about 3:1.

33. The process of claim 32, wherein the molar ratio of the alkali hydroxide base to compound B is about 1.5:1.

34. The process of claim 28, wherein the organic solvent is selected from the group consisting of tetrahydrofuran ("THF"), 2-methyltetrahydrofuran, cyclopentyl methyl ether, tert-butyl methyl ether, 1,2-dimethoxyethane, toluene, hexane, heptane, 1,4-dioxane, and combinations thereof.

35. The process of claim 34, wherein the organic solvent comprises THF.

36. The process of claim 30, wherein the mixture comprising compound B' is stirred for about 1 hour to about 48 hours.

37. The process of claim 1, further comprising quenching the mixture of step (b) with a secondary amine base.

38. The process of claim 37, wherein the secondary amine base is selected from the group consisting of N,N-diethylamine, morpholine, piperidine, pyrrolidine, piperazine, and combinations thereof.

39. The process of claim 1, wherein each admixing step occurs at a temperature in a range of about 0° C. to about 40° C.

40. The process of claim 39, wherein the temperature of each admixing step is in a range of about 15° C. to about 25° C.

* * * * *